(12) United States Patent
Tadayon et al.

(10) Patent No.: US 12,076,315 B2
(45) Date of Patent: *Sep. 3, 2024

(54) STABLE POLYMORPHIC COMPOSITIONS OF BREQUINAR SODIUM AND METHODS OF USE AND MANUFACTURE THEREOF

(71) Applicant: Clear Creek Bio, Inc., Cambridge, MA (US)

(72) Inventors: Abdolsamad Tadayon, Shanghai (CN); Ping Huang, Shanghai (CN); Chaoyi Deng, Shanghai (CN); Jinsuo Yang, Shanghai (CN); Qingqing Lu, Shanghai (CN); Lin Cui, Shanghai (CN); Mo Jia, Shanghai (CN); Xianjun You, Shanghai (CN); David P. Hesson, Malvern, PA (US); Siyi Jiang, Shanghai (CN)

(73) Assignee: Clear Creek Bio, Inc., Cambridge, MA (US)

( * ) Notice: Subject to any disclaimer, the term of this patent is extended or adjusted under 35 U.S.C. 154(b) by 576 days.

This patent is subject to a terminal disclaimer.

(21) Appl. No.: 17/207,518

(22) Filed: Mar. 19, 2021

(65) Prior Publication Data

US 2021/0292280 A1 Sep. 23, 2021

Related U.S. Application Data

(60) Provisional application No. 63/043,382, filed on Jun. 24, 2020, provisional application No. 63/043,388,
(Continued)

(51) Int. Cl.
*C07D 215/52* (2006.01)
*A61K 9/00* (2006.01)
(Continued)

(52) U.S. Cl.
CPC ........ *A61K 31/4704* (2013.01); *A61K 9/0014* (2013.01); *A61K 9/0019* (2013.01);
(Continued)

(58) Field of Classification Search
CPC .............. A61K 31/4704; A61K 9/0014; A61K 9/0019; A61K 31/4015; A61K 31/7056;
(Continued)

(56) References Cited

U.S. PATENT DOCUMENTS

| 3,674,774 A | 7/1972 | Williams et al. |
| 3,802,999 A | 4/1974 | Williams et al. |

(Continued)

FOREIGN PATENT DOCUMENTS

| EP | 3344243 B1 * | 12/2020 | ............. A61K 31/27 |
| WO | 99/32110 A1 | 7/1999 | |

(Continued)

OTHER PUBLICATIONS

Sykes et al. Inhibition of Dihydroorotate Dehydrogenase Overcomes Differentiation Blockade in Acute Myeloid Leukemia, Cell, 167, pp. 171-186, including additional experimental pp. e1-e8 (Year: 2016).*

(Continued)

*Primary Examiner* — Jeffrey S Lundgren
*Assistant Examiner* — Alexander K. Showalter
(74) *Attorney, Agent, or Firm* — Brown Rudnick LLP; Adam M. Schoen

(57) ABSTRACT

The invention provides compositions containing a stable crystalline form of brequinar and methods of making such composition. The invention also provides methods of using such compositions to treat a condition in a subject.

14 Claims, 8 Drawing Sheets

Related U.S. Application Data filed on Jun. 24, 2020, provisional application No. 63/043,384, filed on Jun. 24, 2020, provisional application No. 63/043,386, filed on Jun. 24, 2020, provisional application No. 63/043,380, filed on Jun. 24, 2020, provisional application No. 63/030,677, filed on May 27, 2020, provisional application No. 63/020,460, filed on May 5, 2020, provisional application No. 62/992,720, filed on Mar. 20, 2020.

(51) Int. Cl.
| | |
|---|---|
| A61K 31/47 | (2006.01) |
| A61K 31/4704 | (2006.01) |
| A61K 31/706 | (2006.01) |
| A61K 45/06 | (2006.01) |
| A61P 31/14 | (2006.01) |

(52) U.S. Cl.
CPC ............ *A61K 9/0053* (2013.01); *A61K 31/47* (2013.01); *A61K 31/706* (2013.01); *A61K 45/06* (2013.01); *A61P 31/14* (2018.01); *C07D 215/52* (2013.01); *C07B 2200/13* (2013.01)

(58) Field of Classification Search
CPC .... A61K 9/0053; A61K 31/47; A61K 31/706; A61K 45/06; A61K 2300/00; A61P 31/14; C07D 215/52; C07B 2200/13
See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |
| 4,284,786 | A | 8/1981 | Kammerer et al. |
| 4,451,648 | A | 5/1984 | Parsons et al. |
| 4,680,299 | A | 7/1987 | Hesson |
| 5,032,597 | A | 7/1991 | Hesson |
| 5,523,408 | A | 6/1996 | Batt et al. |
| 5,679,709 | A | 10/1997 | Bartlett et al. |
| 5,807,876 | A | 9/1998 | Armistead et al. |
| 5,945,418 | A | 8/1999 | Bemis et al. |
| 6,093,742 | A | 7/2000 | Salituro et al. |
| 6,214,841 | B1 | 4/2001 | Jackson et al. |
| 6,344,465 | B1 | 2/2002 | Armistead et al. |
| 6,395,763 | B1 | 5/2002 | Stamos et al. |
| 6,399,773 | B1 | 6/2002 | Liu et al. |
| 6,410,540 | B1 | 6/2002 | Goehring et al. |
| 6,420,403 | B1 | 7/2002 | Wanowicz et al. |
| 6,509,363 | B2 | 1/2003 | Salituro et al. |
| 6,518,291 | B1 | 2/2003 | Saunders et al. |
| 6,528,508 | B2 | 3/2003 | Salituro et al. |
| 6,541,496 | B1 | 4/2003 | Armistead et al. |
| 6,613,896 | B1 | 9/2003 | Ramasamy et al. |
| 6,617,323 | B2 | 9/2003 | Iwanowicz et al. |
| 6,617,324 | B1 | 9/2003 | Naraian et al. |
| 6,624,184 | B1 | 9/2003 | Gu et al. |
| 6,632,945 | B2 | 10/2003 | Salituro et al. |
| 6,635,644 | B2 | 10/2003 | Salituro et al. |
| 6,653,309 | B1 | 11/2003 | Saunders et al. |
| 6,825,224 | B2 | 11/2004 | Stamos et al. |
| 6,867,299 | B2 | 3/2005 | Broadhurst et al. |
| 6,919,335 | B2 | 7/2005 | Iwanowicz et al. |
| 6,967,214 | B2 | 11/2005 | Armistead et al. |
| 7,053,111 | B2 | 5/2006 | Gu et al. |
| 7,060,720 | B2 | 6/2006 | Gu et al. |
| 7,087,642 | B2 | 8/2006 | Stamos et al. |
| 7,125,898 | B2 | 10/2006 | Aston et al. |
| 7,135,575 | B2 | 11/2006 | Munson et al. |
| 7,169,779 | B2 | 1/2007 | Salituro et al. |
| 7,205,324 | B2 | 4/2007 | Gu et al. |
| 7,329,681 | B2 | 2/2008 | Armistead et al. |
| 7,423,047 | B2 | 9/2008 | Brookings et al. |
| 7,425,555 | B2 | 9/2008 | Angell et al. |
| 7,427,636 | B2 | 9/2008 | Cannizzaro et al. |
| 7,432,290 | B2 | 10/2008 | Stamos et al. |
| 7,521,447 | B2 | 4/2009 | Munson et al. |
| 7,612,205 | B2 | 11/2009 | Akai et al. |
| 7,638,501 | B1 | 12/2009 | Naviaux |
| 7,642,276 | B2 | 1/2010 | Angell et al. |
| 7,777,069 | B2 | 8/2010 | Stamos et al. |
| 7,989,498 | B2 | 8/2011 | Saunders et al. |
| 8,410,160 | B2 | 4/2013 | Fryszman et al. |
| 8,748,408 | B2 | 6/2014 | Naviaux |
| 8,895,918 | B2 | 11/2014 | Cooks et al. |
| 9,365,639 | B2 | 6/2016 | Robinson et al. |
| 9,546,979 | B2 | 1/2017 | Cooks et al. |
| 9,603,804 | B2 | 3/2017 | Uchida et al. |
| 9,761,426 | B2 | 9/2017 | Cooks et al. |
| 2002/0065296 | A1 | 5/2002 | Dumas et al. |
| 2003/0232877 | A1 | 12/2003 | Sikorski et al. |
| 2004/0224920 | A1 | 11/2004 | Naviaux |
| 2007/0203098 | A1 | 8/2007 | Garlich et al. |
| 2010/0081713 | A1 | 4/2010 | Sharma et al. |
| 2010/0098678 | A1 | 4/2010 | Naviaux |
| 2011/0263620 | A1 | 10/2011 | Hsieh et al. |
| 2014/0031383 | A1 | 1/2014 | Zon et al. |
| 2014/0235556 | A1 | 8/2014 | Halse et al. |
| 2015/0328204 | A1 | 11/2015 | Zon et al. |
| 2016/0046697 | A1 | 2/2016 | Robinson et al. |
| 2017/0119880 | A1 | 5/2017 | Clarke et al. |
| 2019/0209598 | A1 | 7/2019 | Deans et al. |
| 2019/0233539 | A1 | 8/2019 | Johnson et al. |
| 2019/0290634 | A1 | 9/2019 | Kumar et al. |
| 2019/0290635 | A1 | 9/2019 | Kumar et al. |
| 2019/0290892 | A1 | 9/2019 | Kumar et al. |
| 2019/0292154 | A1 | 9/2019 | Kumar et al. |
| 2019/0298670 | A1 | 10/2019 | Glick et al. |
| 2021/0113548 | A1 | 4/2021 | Hesson et al. |
| 2021/0115493 | A1 | 4/2021 | Hesson et al. |

FOREIGN PATENT DOCUMENTS

| | | |
|---|---|---|
| WO | 2000050043 A1 | 8/2000 |
| WO | 2004096287 A2 | 11/2004 |
| WO | 2005117943 A2 | 12/2005 |
| WO | 2008030752 A2 | 3/2008 |
| WO | 2012052180 A1 | 4/2012 |
| WO | 2012109329 A2 | 8/2012 |
| WO | 2013049045 A1 | 4/2013 |
| WO | 2015122995 A1 | 8/2015 |
| WO | 2015169944 A1 | 11/2015 |
| WO | 2017037022 A1 | 3/2017 |
| WO | 2017117372 A1 | 7/2017 |
| WO | 2018038886 A1 | 3/2018 |
| WO | 2018096538 A1 | 5/2018 |
| WO | 2019028171 A1 | 2/2019 |
| WO | 2019/246603 A1 | 12/2019 |
| WO | 2020219423 A1 | 10/2020 |
| WO | 2020236502 A1 | 11/2020 |

OTHER PUBLICATIONS

Mullin, Crystallization (Fourth Edition), published by Butterworth-Heinemann; esp. pp. 86-88, 96, 194-195, and 207. (Year: 2001).*
Wu et al., The Impact of Crystallinity on Brequinar Sodium Hygroscopicity, Pharm. Dev. & Tech., 1 pp. 42-49 (Year: 1996).*
De la Rosa et al., Solubility Determination and Correlation of Warfarin Sodium 2-Propanol Solvate in Pure, Binary, and Ternary Solvent Mixtures, J. Chem. Eng. Data, 64, pp. 1399-1413 (Year: 2019).*
Romao et al., An Efficient and Inexpensive Apparatus for Hot Filtration, J. Chem. Ed., 78, p. 65 (Year: 2001).*
Mullin, Crystallization (Fourth Edition), Butterworth-Heinemann—select pages (Year: 2001).*
Vu, 2017, Regulation of EMT in Colorectal Cancer: A Culprit in Metastasis, Cancers, 9(12):171 (22 pages).
Weber, 2015, Toxicities of Immunotherapy for the Practitioner, Journal of Clinical Oncology, 33(18):2092-2099.

(56) References Cited

OTHER PUBLICATIONS

Weber, 2018, Myeloid-Derived Suppressor Cells Hinder the Anti-Cancer Activity of Immune Checkpoint inhibitors, Front in Immunol. 9:1310 (9 pages).
Werden, 2016, Phosphorylation of serine 367 of FOXC2 by p38 regulates ZEB1 and breast cancer metastasis, without impacting primary tumor growth, Oncogene, 35(46):5977-5988.
Yang, 2016, Downregulation of Foxc2 enhances apoptosis induced by 5-fluorouracil through activation of MAPK and AKT pathways in colorectal cancer, Onc. Letters 11(2):1549-1554.
Yin, 2018, Potential Mechanisms Connecting Purine Metabolism and Cancer Therapy, Front. Immunol., 9:1967 (8 pages).
Zhao, 2004, Measuring changes in tumor oxygenation, Methods Enzymol., 386:378-418.
Levey, 1999, A more accurate method to estimate glomerular filtration rate from serum creatinine: a new prediction equation. Modification of Diet in Renal Disease Study Group, Annals of Internal Medicine, 130(6):461-70.
Levey, 2009, A new equation to estimate glomerular filtration rate, Annals of Internal Medicine, 150(9):604-12.
Lu, 2017, Epithelial-to-Pericyte Transition in Cancer, Cancers, 9(7):77 (13 pages).
Malek, 2004, Effects of the IMPB-dehydrogenase inhibitor, Tiazofurin, in bcr-abl positive acute myelogenous leukemia, Leukemia Research, 28:1125-36.
Mani, 2007, Mesenchyme Forkhead 1 (FOXC2) plays a key role in metastasis and is associated with aggressive pasal-like breast cancers, Proc Natl Acad Sci U S A. 104(24):10069-74.
Mansoori, 2017, The Different Mechanisms of Cancer Drug Resistance: A Brief Review, Adv Pharm Bull, 7(3):339-348.
Maroun, 1993, Multicenter phase II study of brequinar sodium in patients with advanced lung cancer. Cancer Chemother Pharmacol 32:64-66.
Marusyk, 2010, Tumor heterogeneity: causes and consequences, Biochim Biophys Acta. 1805(1):105-17.
Mathew, 2007, Chronic kidney disease and automatic reporting of estimated glomerular filtration rate: revised recommendations, The Medical Journal of Australia, 187(8):459-63.
Mathur, 2017, PTEN Regulates Glutamine Flux to Pyrimidine Synthesis and Sensitivity to Dihydroorotate Dehydrogenase Inhibition, Cancer Discov. 7(4):380-390 (p. 18).
Matsumoto, 2008, Low-field paramagnetic resonance imaging of tumor oxygenation and glycolytic activity in mice, J. Clin. Invest. 118(5):1965-1973 (10 pages).
Mele, 2000, The use of mycophenolate mofetil in transplant recipients, Immunopharmacology, 47:215-245.
Melink, 1985, Phase I Evaluation and Pharmacokinetics of Tiazofurin (2-beta-D-ribofuranosylthiazole-4-carboxamide, NSC 286193), Cancer Res. Jun. 1985;45(6):2859-65.
Miloushev, 2016, Hyperpolarization MRI: Preclinical Models and Potential Applications in Neuroradiology, Top Magn Reson Imaging 25(1):31-37.
Murray, 2013, Assessment of Glomerular Filtration Rate Measurement with Plasma Sampling: A Technical Review, J Nucl Med Technol. 41(2):67-75.
Natale, 1992, Multicenter phase II trial of brequinar sodium in patients with advanced melanoma, Ann Oncol. 3(8):659-60.
Nefedova, 2007, Mechanism of All-Trans Retinoic Acid Effect on Tumor-Associated Myeloid-Derived Suppressor Cells, Cancer Res. 67(22):11021-8.
Noe, 1990, Phase I and pharmacokinetic study of brequinar sodium (NSC368390), Cancer Res., 50(15):4595-99.
Obeng, 1997, Pharmacokinetics of tiazofurin in dogs, Biopharm Drug Dispos. 8(2):125-32.
Ohnesorge, 2005, Quantitation in capillary electrophoresis-mass spectrometry, Electrophoresis. 26 (21): 3973-87.
Paranjape, 2016, Inhibition of FOXC2 restores epithelial phenotype and drug sensitivity in prostate cancer cells with stem-cell properties, Oncogene. 35(46):5963-5976.
Peters, 1990, In vivo inhibition of the pyrimidine de novo enzyme dihydroorotic acid dehydrogenase by brequinar sodium (DUP-785; NSC 368390) in mice and patients, Cancer Res. 50(15):4644-9.
Pitt, 2009, Principles and Applications of Liquid Chromatography-Mass Spectrometry in Clinical Biochemistry, The Clinical Biochemist Reviews, 30(1):19-34.
Popsavin, 2006, Synthesis and antiproliferative activity of two new tiazofurin analogues with 2'-amido functionalities, Bioorg. Med. Chem. Lett. 16(10):2773-2776.
Popsavin, 2011, Antitumour tiazofurin analogues embedded with an amide moiety at the C-2' position, Tetrahedron 67:6847-6858.
Popsavin, 2016, Synthesis and in vitro antitumor activity of tiazofurin analogues with nitrogen functionalities at the C-2' position, European Journal of Medicinal Chemistry 111:114-125.
Preisler, 1987, Comparison of Three Remission Induction Regimens and Two Postinduction Strategies for the Treatment of Acute Nonlymphocytic Leukemia: A Cancer and Leukemia Group B Study, Blood, 69(5):1441-1449.
Rashidi, 2016, Maintenance therapy in acute myeloid leukemia: an evidence-based review of randomized trials, Blood 128(6):763-773.
Roche, 2017, Epigenetic Regulation of the Epithelial to Mesenchymal Transition in Lung Cancer, Cancers, 9(7):E72 (14 pages).
Roche, 2018, The Epithelial-to-Mesenchymal Transition in Cancer, Cancers (Basel). 10(2):E52 (4 pages).
Rose, 1969, Measurement of glomerular filtration rate by inulin clearance without urine collection, BMJ, 2:91-3 (3 pages).
Rule, 2004, Using serum creatinine to estimate glomerular filtration rate: accuracy in good health and in chronic kidney disease, Annals of Internal Medicine, 141(12):929-37.
Rundqvist, 2013, Tumour oxygenation: implications for breast cancer prognosis, Intern Med 274:105-112.
Saleh, 2015, Synthesis of Isatine Derivatives Considering Pfitzinger Reaction Part I, International Journal of Science and Research 4(8):2083-89.
Sangshetti, 2014, Pfitzinger Reaction in the Synthesis of Bioactive Compounds—A Review, Mini-Reviews in Organic Chemistry, 11:1-26.
Schlenk, 2014, Post-remission therapy for acute myeloid leukemia, Haematologica, 99(11):1663-70.
Schwartsmann, 1989, Pharmacokinetics of Brequinar Sodium (NSC 368390) in Patients with Solid Tumors During a Phase I Study, Eur. J. Cancer Clin. Ocol., 25(12):1675-1681.
Schwartsmann, 1990, Phase I study of Brequinar sodium (NSC 368390) in patients with solid malignancies, Cancer Chemother. Pharmacol., 25(5):345-351.
Schwartz, 1976, A simple estimate of glomerular filtration rate in children derived from body length and plasma creatinine, Pediatrics, 58(2):259-63.
Schwartz, 1984, A simple estimate of glomerular filtration rate in full-term infants during the first year of life, The Journal of Pediatrics, 104(6):849-54.
Shvekhgeimer, 2004, The Pfitzinger Reaction (Review). Chemistry of Heterocylcic Compounds 40(3):257-294.
Soveri, 2014, Measuring GFR: A Systematic Review, American Journal of Kidney Diseases. 64(3):411-424.
Swyryd, 1974, N-(Phosphonacetyl)-L-Aspartate, a Potent Transition State Analog Inhibitor of Aspartate Transcarbamylase, Blocks Proliferation of Mammalian Cells in Culture, J. Biol. Chem. 249(21):6945-6950.
Sykes, 2016, Inhibition of Dihydroorotate Dehydrogenase Overcomes Differentiation Blockade in Acute Myeloid Leukemia, Cell, 167:171-186.
Thierauf, 2017, Epithelial-to-Mesenchymal Transition in the Pathogenesis and Therapy of Head and Neck Cancer, Cancers, 9(7):e376 (13 pages).
Tobin, 2018, Targeting myeloid-derived suppressor cells using all-trans retinoic acid in melanoma patients treated with Ipilimumab, Int Immunopharmacol., 63:282-291.
Tricot, 1987, Hematological and biochemical action of tiazofurin (NSC 286193) in a case of refractory acute myeloid leukemia, Cancer Res. 47(18):4988-91.

(56) References Cited

OTHER PUBLICATIONS

Tricot, 1989, Biochemically directed therapy of leukemia with tiazofurin, a selective blocker of inosine 5'-phosphate dehydrogenase activity, Cancer Res. 49(13):3696-701.
Trump, 1985, Phase I clinical study with pharmacokinetic analysis of 2-beta-D-ribofuranosylthiazole-4-carboxamide (NSC 286193) administered as a five-day infusion, Cancer Res. 45(6):2853-58.
Veglia, 2018, Myeloid-derived suppressor cells coming of age, Nat Immunol. 19(2):108-119.
Agostini, 2018, Coronavirus Susceptibility to the Antiviral Remdesivir (GS5734) is Mediated by the Viral Polymerase and the Proofreading Exoribonuclease, MBio, 9(2):1-15.
Amirian, 2020, Current Knowledge about the Antivirals Remdesivir (GS-5734) and GS-441524 as Therapeutic Options for Coronaviruses, One Health, 9(100128):1-7.
Amrutkar, 2017, Pancreatic Cancer Chemoresistance to Gemcitabine, Cancers 9(11):E157 (23 pages).
Andersen, 2019, Novel Antiviral Activities of Obatoclax, Emetine, Niclosamide, Brequinar, and Homoharringtonine, Viruses, 11:1-15.
Angelov, 2009, Blood-Brain Barrier Disruption and Intra-Arterial Methotrexate-Based Therapy for Newly Diagnosed Primary CNS Lymphoma: A Multi-Institutional Experience, J Clin Oncol 27(21):3503-9 (8 pages).
Arteaga, 1989, Phase I Clinical and Pharmacokinetic Trial of Brequinar Sodium (DUP 785; NSC 368390), Cancer Research, 49:4648-53.
Ball, 2008, Acute GvHD: pathogenesis and classification, Bone Marrow Transplantation 41:S58-S64.
Batist, 1985, Phase I and pharmacokinetic study of tiazofurin (TCAR, NSC 286193) administered by continuous Infusion. Invest New Drugs. 3(4):349-55.
Bennett, 1976, Proposals for the classification of the acute leukaemias. French-American-British (FAB) co-operative group Br. J. Haematol. 33 (4):451-8.
Bennett, 1989, Proposals for the classification of chronic (mature) B and T lymphoid leukaemias. French-American-British (FAB) Cooperative Group J. Clin. Pathol. 42 (6):567-84.
Blackwell, 2017, The Role of Cancer-Derived Exosomes in Tumorigenicity & Epithelial-to-Mesenchymal Transition, Cancers, 9(8):105 (11 pages).
Bork, 1989, A Phase I Clinical and Pharmacokinetic Study of Brequinar Sodium, DUP 785 (NW 368390), Using a Weekly and a Biweekly Schedule, Eur J Cancer Clin Oncol, 25(10):1403-1411.
Bouchlaka, 2010, Immunotherapy following hematopoietic stem cell transplantation: potential for synergistic effects, Immunotherapy. 2(3):399-418.
Boven, 1992, The anti-tumour effects of the prodrugs N-l-leucyl-doxorubicin and vinblastine-isoleucinate in human ovarian cancer xenografts, Br J Cancer. 66(6):1044-7.
Bruneau, 1998, Purification of human dihydro-orotate dehydrogenase and its inhibition by A77 1726, the active metabolite of leflunomide. Biochem J. 336(2):299-303.
Buj, 2018, Deoxyribonucleotide Triphosphate Metabolism in Cancer and Metabolic Disease, Front. Endocrinol. 9:177 (10 pages).
Burris, 1998, Pharmacokinetic and phase I studies of brequinar (DUP 785; NSC368390) in combination with cisplatin in patients with advanced malignancies, Invest. New Drugs, 16(1):19-27.
Chen, 1990, Structure-activity relationship of quinoline carboxylic acids. A new class of inhibitors of dihydroorotate dehydrogenase, Biochem. Pharmacol. 40:709-714.
Cho, 2017, Noninvasive Interrogation of Cancer Metabolism with Hyperpolarized 13C MRI, J Nucl Med 58:1201-1206.
Cuny, 2017, Inosine-5'-monophosphate dehydrogenase (IMPDH) inhibitors: a patent and scientific literature review (2002-2016), Expert Opin Ther Pat., 27(6):677-690.
Darvin, 2018, Immune checkpoint inhibitors: recent progress and potential biomarkers, Exp Mol Med. 50(12):165 (11 pages).

Dexter, 1985, Activity of a Novel 4-Quinolinecarboxylic Acid, NSC 368390 [6-Fluoro-2-(2'-fluoro-1,1'-biphenyl-4-yl)-3-methyl-4-quinolinecarboxylic Acid Sodium Salt], against Experimental Tumors, Cancer Research, 45:5563-5568.
Di Gialleonardo, 2016, The Potential of Metabolic Imaging, Semin Nucl Med. 46(1):28-39.
Falini, 2010, New classification of acute myeloid leukemia and precursor-related neoplasms: changes and unsolved issues Discov Med. 10(53):281-92.
Fedele, 2017, The Epithelial-to-Mesenchymal Transition in Breast Cancer: Focus on Basal-Like Carcinomas, Cancers, 9(10):E134 (19 pages).
Foo, 2014, Evolution of acquired resistance to anti-cancer therapy, J Theor Biol. 0:10-20 (24 pages).
Fu, 2017, The Emerging Role of Polo-Like Kinase 1 in Epithelial-Mesenchymal Transition and Tumor Metastasis, Cancers, 9(10):131 (15 pages).
Gaianigo, 2017, EMT and Treatment Resistance in Pancreatic Cancer, Cancers, 9(9):122 (17 pages).
Gebeyehu, 1985, Ribavirin, Tiazofurin, and Selenazofurin: Mononucleotides and Nicotinamide Adenine Dinucleotide Analogues. Synthesis, Structure, and Interactions with IMP Dehydrogenase, J. Med. Chem. 28:99-105.
Gnanamony 2017, Chemoresistance in pancreatic cancer: Emerging concepts, Oncology Letters 13:2507-2513.
Green, 1986, Clinical pharmacology of tiazofurin (2-ß-D-ribofuranosylthiazole-4-carboxamide, NSC 286193), Invest New Drugs 4:387-394.
Grelet, 2017, Pleiotropic Roles of Non-Coding RNAs in TGF-ß-Mediated Epithelial-Mesenchymal Transition and Their Functions in Tumor Progression, Cancers, 9(7):75 (15 pages).
Grem, 1990, Clinical toxicity associated with tiazofurin, Invest New Drugs. 8(2):227-38.
Groenendijk, 2014, Drug resistance to targeted therapies: Deja vu all over again, Mol. Oncol. 8:1067-1083 (17 pages).
Henriksen, 2015, The clearance concept with special reference to determination of glomerular filtration rate in patients with fluid retention, Clinical Physiology and Functional Imaging, 35(1):7-16.
Hsu, 2011, Measured GFR as Gold Standard—All that Glitters Is Not Gold?, Clinical Journal of the American Society of Nephrology, 6(8):1813-1814.
International Search Report and Written Opinion issued in International Application No. PCT/US2021/023350, date of mailing: Jun. 8, 2021 (9 pages).
International Search Report and Written Opinion issued in International Patent Application No. PCT/US2019/023983, date of mailing: Jul. 17, 2019 (12 pages).
International Search Report and Written Opinion issued in International Patent Application No. PCT/US2021/023351, date of mailing: Jul. 12, 2021 (20 pages).
International Search Report issued in International Application No. PCT/US2021/023350, date of mailing: Jun. 8, 2021, 9 pages.
Jayaram, 1992, Int J Cancer, Clinical Pharmacokinetic Study of Tiazofurin Administered as a 1-hour infusion 51:182-188.
Joshi, 1997, Phase I Safety and Pharmacokinetic Studies of Brequinar Sodium after Single Ascending Oral Doses in Stable Renal, Hepatic, and Cardiac Allograft Recipients, J Clin Pharmacol, 37:1121-1128.
Kanu, 2008, Ion mobility-mass spectrometry, Journal of Mass Spectrometry, 43 (1):1-22.
Kiewe, 2007, High-dose methotrexate is beneficial in parenchymal brain masses of uncertain originsuspicious for primary CNS lymphoma, Neuro Oncol. 9(2):96-102.
Kitchin, 1997, Rediscovering mycophenolic acid: A review of its mechanism, side effects, and potential uses Journal of the American Academy of Dermatology. 37(3):445-449.
Klymenko, 2017, Complex Determinants of Epithelial: Mesenchymal Phenotypic Plasticity in Ovarian Cancer, Cancers, 9(8):104 (32 pages).
Kolch, 2005, Capillary electrophoresis-mass spectrometry as a powerful tool in clinical diagnosis and biomarker discovery, Mass Spectrom Rev. 24 (6):959-77.

(56) References Cited

OTHER PUBLICATIONS

Koundinya, 2018, Dependence on the Pyrimidine Biosynthetic Enzyme DHODH Is a Synthetic Lethal Vulnerability in Mutant KRAS-Driven Cancers, Cell Chem Biol., 25(6):705-717.e11 (34 pages).
Lee, 2014, Current concepts in the diagnosis and management of cytokine release syndrome, (2014) Blood 124 (2):188-195.
Legras, 2017, Epithelial-to-Mesenchymal Transition and MicroRNAs in Lung Cancer, Cancers, 9(8):101 (29 pages).

* cited by examiner

STABLE POLYMORPHIC COMPOSITIONS OF BREQUINAR SODIUM AND METHODS OF USE AND MANUFACTURE THEREOF

FIELD OF THE INVENTION

The invention relates generally to pharmaceutical compositions that contain crystalline forms of brequinar sodium salt, methods of making such compositions, and methods of using such compositions to treat a condition in a subject.

BACKGROUND

Brequinar is a compound that acts as a potent and selective inhibitor of the enzyme dihydroorotate dehydrogenase (DHODH), an enzyme required for pyrimidine synthesis. The drug blocks synthesis of pyrimidine-based nucleotides in the body and so inhibits cell growth. Brequinar has been investigated for numerous different indications.

SUMMARY

The invention recognizes that crystals of brequinar sodium salt exist in multiple polymorphic forms and that one of those forms, polymorphic form C, is most stable under ambient conditions. Therefore, the stable crystalline form of brequinar sodium salt described herein allows the drug to be formulated in pharmaceutical compositions (for example solid pharmaceutical compositions for oral administration) amenable to commercial production and distribution. Prior to the insight of this invention, manufacture of crystalline brequinar sodium salt was deemed too unpredictable for large-scale manufacture, such as for example manufacture of solid oral dosage forms (e.g., such as tablets and capsules). The compositions of the invention overcome prior stability and consistency issues in the manufacturing process to provide the most stable form of brequinar sodium. The polymorphic form of brequinar sodium salt described herein enables the manufacture and distribution of solid dosage forms that can be easily self-administered by patients. The invention also provides methods of making crystals of polymorphic form C of brequinar sodium salt. The invention also provides methods of using compositions containing polymorphic form C of brequinar sodium salt to treat various conditions. Of note, the polymorphic form C of brequinar sodium salt can be formulated in any type of pharmaceutical formulation for any route of delivery.

In an aspect, the invention provides crystals containing polymorphic form C of brequinar sodium salt. The polymorphic form C of may contain a brequinar sodium salt hydrate. In another aspect, the invention provides pharmaceutical compositions containing a solid form of brequinar sodium salt, wherein at least 75% of the brequinar sodium salt is polymorphic form C. The composition may contain a solid form of brequinar sodium salt in which at least 80%, at least 85%, at least 90%, at least 95%, at least 96%, at least 97%, at least 98%, at least 99%, or at least 99.5% of the brequinar sodium salt is polymorphic form C. The polymorphic form C of brequinar sodium salt may contain a brequinar sodium salt hydrate. The composition may be formulated for administration via a particular route. For example, the composition may be formulated for oral, intravenous, enteral, parenteral, dermal, buccal, topical, transdermal, subcutaneous, nasal, or pulmonary administration. The composition may be formulated for administration by injection or with or on an implantable medical device.

In another aspect, the invention provides methods of treating a condition in a subject by providing to a subject having the condition a pharmaceutical composition containing a brequinar sodium salt, wherein at least 75% of the brequinar sodium salt is polymorphic form C. The method may include providing a composition that contains the brequinar sodium salt in which at least 80%, at least 85%, at least 90%, at least 95%, at least 96%, at least 97%, at least 98%, at least 99%, or at least 99.5% of the brequinar sodium salt is polymorphic form C. The polymorphic form C of brequinar sodium salt may contain a brequinar sodium salt hydrate. The compositions containing polymorphic form C of brequinar sodium salt may be administered in as any type of pharmaceutical composition suitable for any route of administration. The composition may be provided orally, intravenously, enterally, parenterally, dermally, buccally, topically, transdermally, by injection, subcutaneously, nasally, pulmonarily, or with or on an implantable medical device.

The compositions described herein may be used to treat any condition for brequinar has been associated with for us, such as cancer or viral infections or an autoimmune disorder. In certain embodiments, the condition may be a viral infection. The viral infection may include an adenovirus, coronavirus, enterovirus, human metapneumovirus, human parainfluenza virus, human respiratory syncytial virus, influenza virus, or rhinovirus. The coronavirus may be Middle East respiratory syndrome coronavirus (MERS-COV), severe acute respiratory syndrome coronavirus (SARS-COV), or severe acute respiratory syndrome coronavirus 2 (SARS-COV-2). The influenza virus may be influenza A, influenza B, influenza C, or influenza D. The influenza A virus may be a H1N1, H3N2, N9N2, or H5N1 strain. The infection may affect a particular tissue, organ, or system. The infection may affect one or more of the alveoli, bronchi, bronchioles, larynx, lungs, nasal cavities, nose, pharynx, respiratory system, sinuses, and trachea.

In other embodiments, the condition may be cancer. The cancer may be acute lymphoblastic leukemia, acute myeloid leukemia, adult T cell leukemia/lymphoma, bladder cancer, breast cancer, cervical cancer, colorectal cancer, gastric cancer, glioblastoma, glioma, head and neck cancer, kidney cancer, leukemia, liver cancer, lung cancer, lymphoma, melanoma, Merkel cell carcinoma, myeloma, osteosarcoma, ovarian cancer, pancreatic cancer, prostate cancer, thyroid cancer, or uterine cancer.

The condition may be an autoimmune disorder. The autoimmune disorder may be arthritis, hepatitis, chronic obstructive pulmonary disease, multiple sclerosis, or tendonitis.

In another aspect, the invention provides methods of making a crystal containing polymorphic form C of brequinar sodium salt, the methods including the steps of combining a solid form of brequinar acid, sodium hydroxide (NaOH), and a solvent to produce a solution and crystallizing brequinar sodium salt from the solution to produce a crystal comprising polymorphic form C of brequinar sodium salt. The polymorphic form C of brequinar sodium salt may contain a brequinar sodium salt hydrate.

The solvent may contain isopropanol, water, or both. The solvent may contain isopropanol and water in a defined ratio. The solvent may contain isopropanol and water in a ratio of from about 90:10 to about 99:1, from about 92:8 to about 99:1, from about 95:5 to about 99:1, from about 96:4 to about 99:1, from about 97:3 to about 99:1, from about 90:10 to about 98:2, from about 92:8 to about 98:2, from about 95:5 to about 98:2, from about 96:4 to about 98:2, from about 97:3 to about 98:2, about 95:5, about 96:4, about 97:3, or about 98:2.

The solid form of brequinar acid may be combined with NaOH at a defined ratio. The NaOH and solid form of brequinar acid may be combined at from about 0.25 to about 4.0, from about 0.5 to about 4.0, from about 0.75 to about 4.0, from about 1.0 to about 4.0, from about 0.25 to about 2.0, from about 0.5 to about 2.0, from about 0.75 to about 2.0, from about 1.0 to about 2.0, from about 0.25 to about 1.6, from about 0.5 to about 1.6, from about 0.75 to about 1.6, from about 1.0 to about 1.6, from about 0.25 to about 1.3, from about 0.5 to about 1.3, from about 0.75 to about 1.3, from about 1.0 to about 1.3, from about 0.25 to about 1.1, from about 0.5 to about 1.1, from about 0.75 to about 1.1, from about 1.0 to about 1.1, about 1.0, about 1.05, or about 1.1 molar equivalents.

The combining step may include incubating the combined brequinar acid, NaOH, and solvent at from about 60° C. to about 90° C., from about 65° C. to about 90° C., from about 70° C. to about 90° C., from about 73° C. to about 90° C., from about 60° C. to about 85° C., from about 65° C. to about 85° C., from about 70° C. to about 85° C., from about 73° C. to about 85° C., from about 60° C. to about 80° C., from about 65° C. to about 80° C., from about 70° C. to about 80° C., from about 73° C. to about 80° C., from about 60° C. to about 77 °C, from about 65° C. to about 77° C., from about 70° C. to about 77 °C, from about 73° C. to about 77° C., about 73° C., about 75° C., or about 77° C.

The combining step may include removing insoluble material from the solution or the combined brequinar acid, NaOH, and solvent. Insoluble material may be removed by filtration.

The combining step may include incubating the combined brequinar acid, NaOH, and solvent at from about 50° C. to about 70° C., from about 55° C. to about 70° C., from about 50° ° C. to about 65° C., from about 55° C. to about 65° C., about 55° C., about 60° C., or about 65° C.

The combining step may include two or more of the aforementioned steps performed in a particular sequence. The combining step may include two or more of the following steps performed in the following sequence: incubating the combined brequinar acid, NaOH, and solvent at a first temperature; removal of insoluble material; and incubating the combined brequinar, NaOH, and solvent at a second temperature, which may be lower than the first temperature.

The crystallizing step may include adding a seed crystal of polymorphic form C of brequinar sodium salt to the solution to produce a seeded mixture. The crystallizing step may include incubating the seeded mixture at from about 15° C. to about 35° C., from about 20° C. to about 35° C., from about 15° C. to about 30° C., from about 20° C. to about 30° C., about 20° C. about 25° C., or about 30° C. The crystallizing step may include adding an alkane to the solution or seeded mixture to produce an alkane-containing mixture. The alkane may be n-heptane. The crystallizing step may include incubating the alkane-containing mixture for a defined period. The crystallizing step may include incubating the alkane-containing mixture for from about 6 hours to about 24 hours. The crystallizing step may include removing the solvent from the polymorphic form C of brequinar sodium salt. Removing the solvent may include filtering the polymorphic form C of brequinar sodium salt, drying the polymorphic form C of brequinar sodium salt, or both.

The crystallizing step may include two or more of the aforementioned steps performed in a particular sequence. The crystallizing step may include two or more of the following steps performed in the following sequence: adding a seed crystal of polymorphic form C of brequinar sodium salt to the solution to produce a seeded mixture; incubating the seeded mixture at a defined temperature; adding an alkane to the solvent or the seeded mixture; incubating the alkane-containing mixture for a defined period; and removing the solvent from the polymorphic form C of brequinar sodium salt.

DETAILED DESCRIPTION

Figure 1:
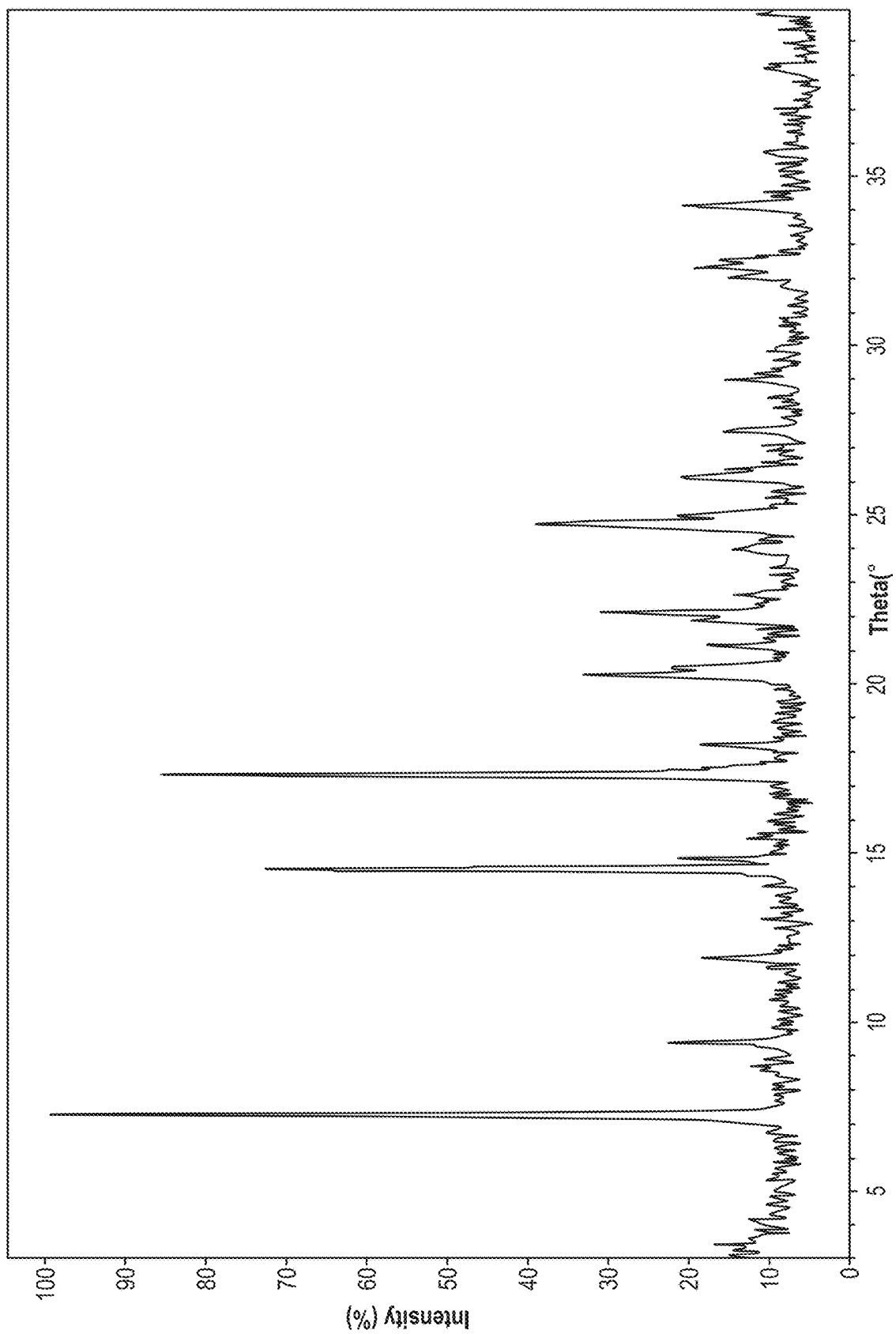
FIG. 1 is an X-ray powder diffraction (XRPD) pattern of brequinar sodium salt from batch PS04375-1-E-P4.
Figure 2:
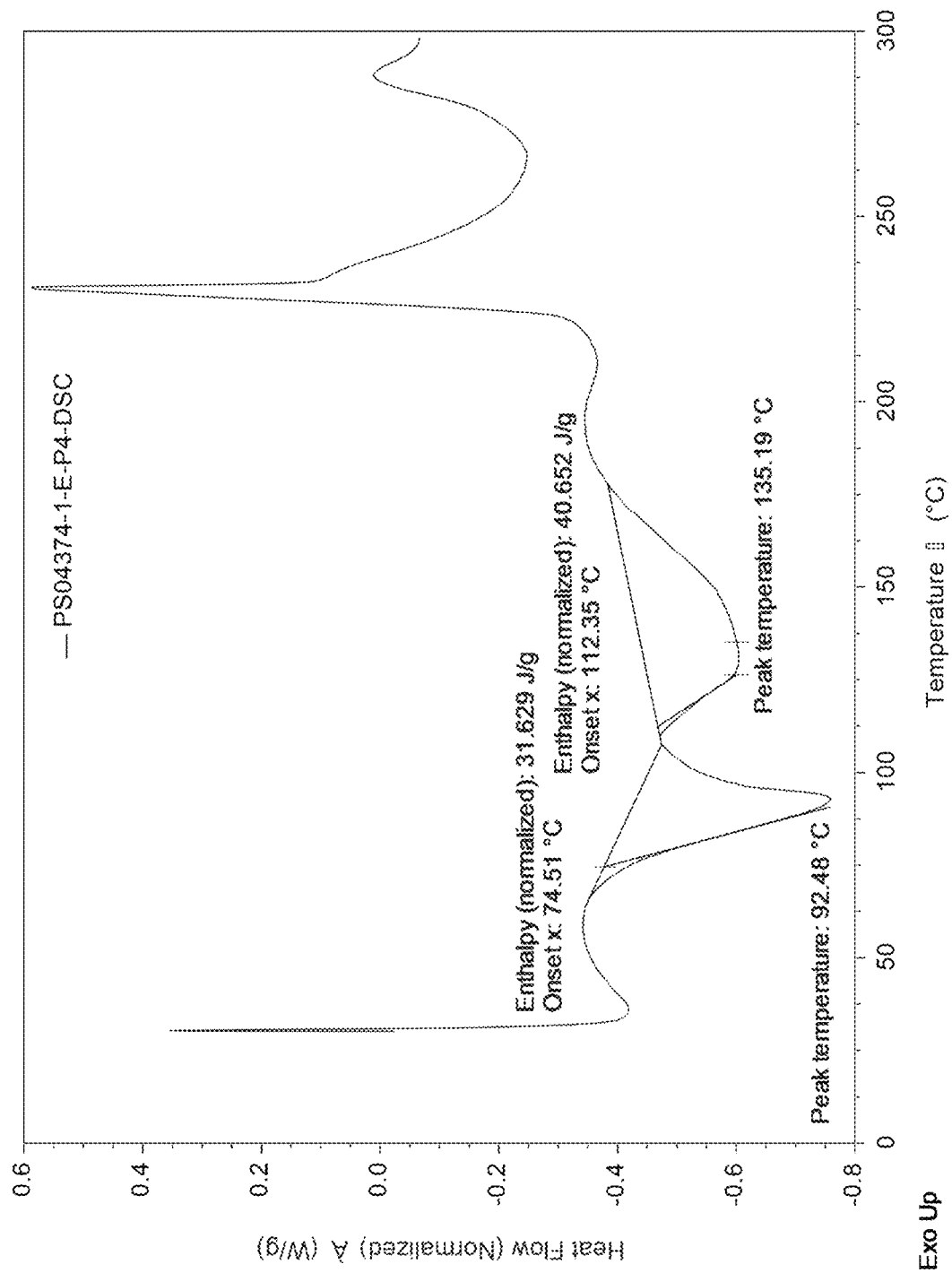
FIG. 2 is a differential scanning calorimetry (DSC) thermogram of brequinar sodium salt from batch PS04375-1-E-P4.
Figure 3:
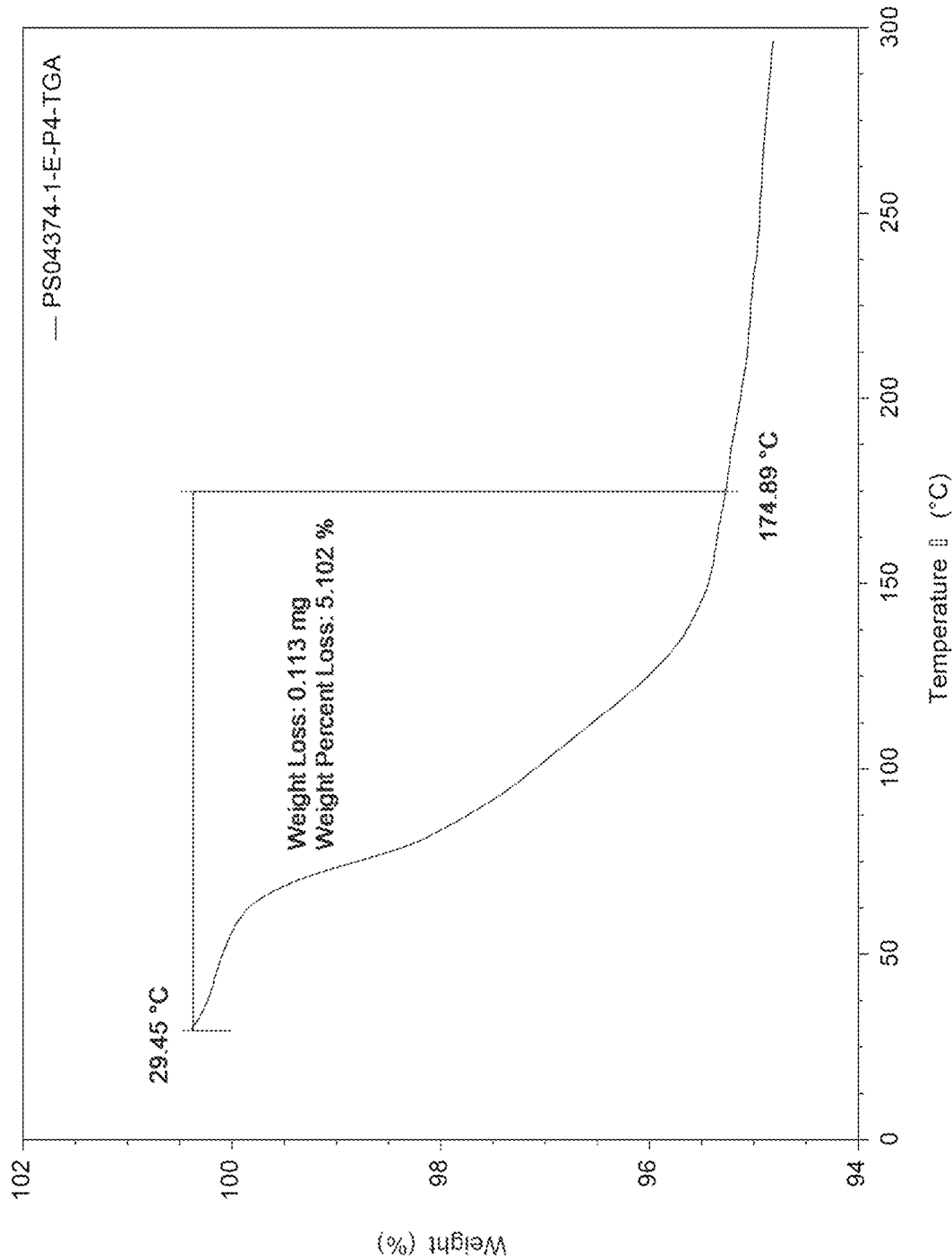
FIG. 3 is a thermogravimetric analysis (TGA) thermogram of brequinar sodium salt from batch PS04375-1-E-P4.
Figure 4:
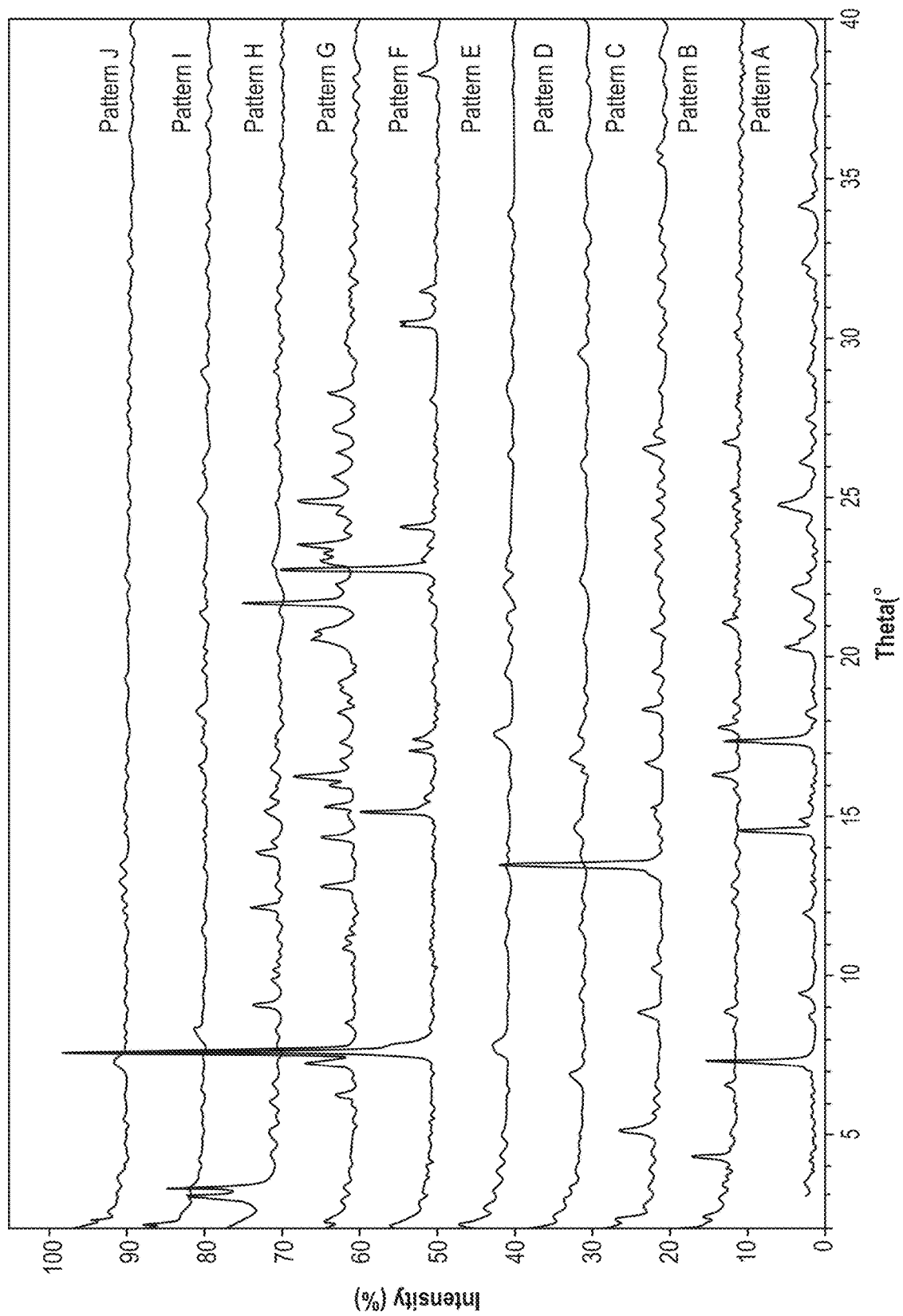
FIG. 4 is an overlay of XRPD scans Patterns A-J of brequinar sodium salt from batch PS04375-1-E-P4.

Brequinar has been investigated as a therapeutic candidate to treat a variety of conditions. Although brequinar was identified more than 30 years ago, one limitation on its therapeutic utility has been the difficulty of formulating the compound for commercial scale manufacturing and production. The invention overcomes that problem by identifying a crystal form of brequinar sodium salt that is stable and consistently reproducible in commercial manufacturing processes. The invention recognizes that crystals of brequinar sodium salt may exist in a variety of polymorphic forms and that only one of those forms, polymorphic form C, is stable under ambient conditions. The invention also provides methods of producing crystals containing the polymorphic form C of brequinar sodium salt. Thus, the compositions and methods of the invention permit the production of stable solid forms of brequinar sodium that are suitable for large-scale manufacture, distribution, and storage. The compositions herein can be formulated for any pharmaceutical composition for any route of administration.

Compositions Containing Polymorphic Form C of Brequinar Sodium Salt

The invention provides crystals of the polymorphic form C of brequinar sodium salt and pharmaceutical compositions containing such crystals. Brequinar has the systematic name 6-fluoro-2-(2'-fluoro-1,1' biphenyl-4-yl)-3-methyl-4-quinoline carboxylic acid and the following structure:

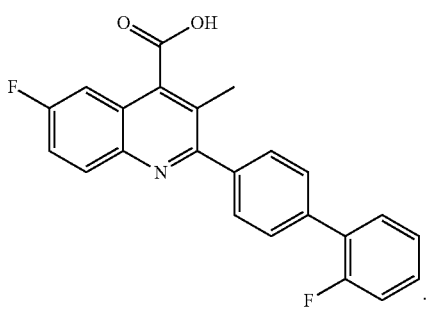 [SMILES: Cc1c(-c2ccc(-c3ccccc3F)cc2)nc2ccc(F)cc2c1C(=O)O]

Brequinar and related compounds are described in, for example, U.S. Pat. Nos. 4,680,299 and 5,523,408, the contents of which are incorporated herein by reference.

Brequinar is an inhibitor of dihydroorotate dehydrogenase (DHODH), a key enzyme involved in pyrimidine synthesis. DHODH converts dihydroorotate (DHO) to orotate, and inhibition of DHODH activity leads to accumulation of DHO. Because cell membranes are permeable to DHO, inhibiting DHODH in the body results in elevated levels of DHO in the blood and other body fluids. Therefore, the activity of brequinar on its target can be monitored in vivo by analysis of DHO levels in body fluid samples. The use of metabolites, such as DHO, to evaluate in vivo target engagement of DHODH inhibitors, such as brequinar, is known in the art and described in, for example, International Patent Publication Nos. WO 2019/191030 and WO 2019/191032, the contents of which are incorporated herein by reference.

Crystals of brequinar sodium salt exist in several different polymorphic forms. As described in more detail in the Examples, the inventors have identified ten distinct X-ray powder diffraction (XRPD) patterns in crystals of brequinar sodium salt, Patterns A-J. Seven of the patterns, Patterns B, D, E, F, G, I and J, represent unstable polymorphic forms that spontaneously convert to polymorphic form C under conditions of ambient temperature and humidity. Pattern A represents a metastable form that also changes into other forms over time when stored at ambient conditions. In contrast, the polymorphic form C is stable under ambient conditions. Consequently, polymorphic form C of brequinar sodium salt is the most desirable for use in solid oral dosage formulations, such as tablets, because it retains its density and is not prone to swelling or shrinkage during manufacture, distribution, and storage of the drug.

In crystals containing polymorphic form C of brequinar sodium salt, the crystals may contain brequinar sodium salt hydrate.

In pharmaceutical compositions of the invention, the composition may contain all or nearly all of the brequinar sodium salt in polymorphic form C. For example and without limitation, the composition may contain a brequinar sodium salt in which at least 75%, at least 80%, at least 85%, at least 90%, at least 95%, at least 96%, at least 97%, at least 98%, at least 99%, or at least 99.5% of the brequinar sodium salt is polymorphic form C.

The composition may be formulated for administration via any route. For example and without limitation, the composition may be formulated for oral, intravenous, enteral, parenteral, dermal, buccal, topical, transdermal, subcutaneous, nasal, or pulmonarily administration. The composition may be formulated for administration by injection or with or on an implantable medical device. For example and without limitation, the composition for oral administration may be formulated as a caplet, capsule, pill, or tablet.

Compositions intended for oral use may be prepared according to any method known in the art for the manufacture of pharmaceutical compositions and such compositions may contain one or more agents selected from sweetening agents, flavoring agents, coloring agents, and preserving agents, in order to provide pharmaceutically elegant and palatable preparations. Tablets contain the compounds in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc.

The tablets may be uncoated, or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452 and 4,265,874, to form osmotic therapeutic tablets for control release. Preparation and administration of compounds is discussed in U.S. Pat. No. 6,214,841 and U.S. Pub. No. 2003/0232877, the contents of each of which are incorporated by reference herein.

Formulations for oral use may also be presented as hard gelatin capsules in which the compounds are mixed with an inert solid diluent, for example calcium carbonate, calcium phosphate or kaolin.

Pharmaceutical compositions may include other pharmaceutically acceptable carriers, such as sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; or excipients.

The pharmaceutically acceptable carrier may be an encapsulation coating. For example, the encapsulation coating may contain carrageenan, cellulose acetate phthalate, cellulose acetate succinate, cellulose acetate trimellitate, collagen, gelatin, hydroxypropyl methyl cellulose acetate, a methyl acrylate-methacrylic acid copolymer, polyvinyl acetate phthalate shellac, sodium alginate, starch, or zein.

The composition may be formulated for a non-oral route of administration. For example and without limitation, the composition may be formulated for intravenous, enteral, parenteral, dermal, buccal, topical, transdermal, subcutaneous, nasal, or pulmonary administration. The composition may be formulated for administration by injection or with or on an implantable medical device.

The composition may be formulated for direct non-oral administration. Alternatively, the composition may be formulated to be mixed, dissolved, or converted to another format prior to administration. For example and without limitation, brequinar may administered as a solution, suspension, emulsion, cream, paste, ointment, or any other format suitable for non-oral administration.

The composition may be formulated for single unit dosage. The composition may be formulated for a divided dosage.

Methods of Making Crystals of Polymorphic Form C of Brequinar Sodium Salt

The invention provides methods of making a crystal containing polymorphic form C of brequinar sodium salt. The methods include the steps combining a solid form of brequinar acid, sodium hydroxide (NaOH), and a solvent to produce a solution and crystallizing brequinar from the solution to produce a crystal of the polymorphic form C of brequinar sodium salt. As discussed in more detail below, the methods may include additional steps, and the aforementioned steps may include steps or sub-steps within them.

The solvent may contain an organic solvent, water, or both. The organic solvent may be an alcohol, such as ethanol or isopropanol. The solvent may contain an alcohol, such as isopropanol, and water in a defined ratio. For example and without limitation, the solvent may contain isopropanol and water in a ratio of from about 90:10 to about 99:1, from about 92:8 to about 99:1, from about 95:5 to about 99:1, from about 96:4 to about 99:1, from about 97:3 to about 99:1, from about 90:10 to about 98:2, from about 92:8 to about 98:2, from about 95:5 to about 98:2, from about 96:4 to about 98:2, from about 97:3 to about 98:2, about 95:5, about 96:4, about 97:3, or about 98:2.

To facilitate dissolving of the sold brequinar acid in the solvent, a strong base, such as NaOH, may be added to the mixture. The solid form of brequinar acid may be combined with NaOH at a defined ratio. For example and without limitation, the NaOH and solid form of brequinar may be combined at from about 0.25 to about 4.0, from about 0.5 to about 4.0, from about 0.75 to about 4.0, from about 1.0 to about 4.0, from about 0.25 to about 2.0, from about 0.5 to about 2.0, from about 0.75 to about 2.0, from about 1.0 to about 2.0, from about 0.25 to about 1.6, from about 0.5 to about 1.6, from about 0.75 to about 1.6, from about 1.0 to about 1.6, from about 0.25 to about 1.3, from about 0.5 to about 1.3, from about 0.75 to about 1.3, from about 1.0 to about 1.3, from about 0.25 to about 1.1, from about 0.5 to about 1.1, from about 0.75 to about 1.1, from about 1.0 to about 1.1, about 1.0, about 1.05, or about 1.1 molar equivalents.

To facilitate dissolving of the solid brequinar acid in the solvent, the mixture may be heated, i.e., incubated at a first defined temperature. For example and without limitation, the mixture may be incubated at from about 60° C. to about 90° C., from about 65° C. to about 90° C., from about 70° C. to about 90° C., from about 73° C. to about 90° C., from about 60° C. to about 85° C., from about 65° C. to about 85° C., from about 70° C. to about 85° ° C., from about 73° C. to about 85° C., from about 60° C. to about 80° C., from about 65° C. to about 80° C., from about 70° C. to about 80° C., from about 73° C. to about 80° C., from about 60° C. to about 77° C., from about 65° C. to about 77° C., from about 70° C. to about 77° C., from about 73° C. to about 77° C. about 73° C., about 75° C., or about 77° C.

It may be necessary to remove insoluble material from the mixture. For example, insoluble material may be removed by filtration.

Following heating and/or filtration, the mixture or solution may be cooled, i.e., incubated at a second defined temperature that is lower than the first defined temperature. For example and without limitation, the solution may be incubated at from about 50° ° C. to about 70° C., from about 55° C. to about 70° C., from about 50° C. to about 65° C., from about 55° C. to about 65° C., about 55° C., about 60° C., or about 65° C.

The aforementioned steps involved in making the brequinar solution may be performed in a specific sequence. For example and without limitation, two or more of the steps may be performed in the following sequence: mixing the solid form of brequinar acid and the solvent, optionally including the strong base, such as NaOH; heating the mixture by incubating it at a first temperature as described above; removing insoluble material from the mixture; and cooling the mixture by incubating it at a second temperature as described above.

The crystallizing step may include adding a seed crystal of polymorphic form C of brequinar sodium salt to the solution to produce a seeded mixture.

The crystallizing step may include incubating the seeded mixture at a defined temperature. For example and without limitation, the seeded mixture may be incubated at from about 15° C. to about 35° C., from about 20° ° C. to about 35° C., from about 15° C. to about 30° C., from about 20° C. to about 30° C., about 20° C., about 25° C., or about 30° C.

The crystallizing step may include adding an agent that facilitates precipitation of the brequinar sodium salt. The agent may be an organic compound, such as an alkane. The alkane may be n-heptane.

The crystallizing step may include incubating the alkane-containing mixture for a defined period. The crystallizing step may include incubating the alkane-containing mixture for from about 6 hours to about 24 hours.

The crystallizing step may include removing the solvent from the precipitated brequinar sodium salt. Removing the solvent may include filtering the brequinar sodium salt, drying the brequinar sodium salt, or both.

The crystallizing step may include two or more of the aforementioned steps performed in a particular sequence. For example and without limitation, two or more of the steps may be performed in the following sequence: adding a seed crystal of polymorphic form C of brequinar sodium salt to the solution to produce a seeded mixture; incubating the seeded mixture at a defined temperature; adding an alkane to the seeded mixture; incubating the alkane-containing mixture for a defined period; and removing the solvent from the polymorphic form C of brequinar.

Further details on preparation of the polymorphic form C of brequinar are described in the Examples.

Methods of Treating Conditions with Polymorphic Form C of Brequinar

Conditions

The invention provides methods of treating a condition in subject by providing to the subject a composition containing polymorphic form C of brequinar sodium salt. The condition may be any disease, disorder, or condition for which brequinar provides a therapeutic benefit.

The condition may be a cancer. The cancer may include a solid tumor or hematological tumor. For example and without limitation, the cancer may be acute lymphoblastic leukemia (ALL), acute myeloid leukemia (AML), adult T cell leukemia/lymphoma (ATLL), bladder cancer, breast cancer, such as triple negative breast cancer (TNBC), cervical cancer, colorectal cancer, gastric cancer, glioblastoma, glioma, head and neck cancer, kidney cancer, leukemia, liver cancer, lung cancer, such as small cell lung cancer and non-small cell lung cancer, lymphoma, melanoma, Merkel cell carcinoma, myeloma, such as multiple myeloma, osteosarcoma, ovarian cancer, pancreatic cancer, prostate cancer, thyroid cancer, or uterine cancer.

In AML, myeloblasts arrested in an early stage of differentiation proliferate in an uncontrolled manner and interfere with the development of other blood cells in the bone marrow. Inhibitors of dihydroorotate dehydrogenase (DHODH) cause differentiation of myeloblasts and prevent their leukemia-initiating activity. The role of DHODH in AML is described in Sykes et al., Inhibition of Dihydroorotate Dehydrogenase Overcomes Differentiation Blockade in Acute Myeloid Leukemia, Cell 167, 171-186, Sep. 22, 2016; dx.doi.org/10.1016/j.cell.2016.08.057, the contents of which are incorporate herein by reference.

The condition may be or include one or more subtypes of AML. AML cases are classified based on cytological, genetic, and other criteria, and AML treatment strategies vary depending on classification. One AML classification system is provided by the World Health Organization (WHO). The WHO classification system includes subtypes of AML provided in Table 1 and is described in Falini B, et al. (October 2010) "New classification of acute myeloid leukemia and precursor-related neoplasms: changes and unsolved issues" Discov Med. 10 (53): 281-92, PMID 21034669, the contents of which are incorporated herein by reference.

TABLE 1

| Name | Description |
|---|---|
| Acute myeloid leukemia with recurrent genetic abnormalities | Includes:<br>AML with translocations between chromosome 8 and 21—[t(8;21)(q22;q22);] RUNX1/RUNX1T1; (ICD-O 9896/3);<br>AML with inversions in chromosome 16—[inv(16)(p13.1q22)] or internal translocations in it—[t(16;16)(p13.1;q22);] CBFB/MYH11; (ICD-O 9871/3);<br>Acute promyelocytic leukemia with translocations between chromosome 15 and 17—[t(15;17)(q22;q12);] RARA/PML; (ICD-O 9866/3);<br>AML with translocations between chromosome 9 and 11—[t(9;11)(p22;q23);] MLLT3/MLL;<br>AML with translocations between chromosome 6 and 9—[t(6;9)(p23;q34);] DEK/NUP214;<br>AML with inversions in chromosome 3—[inv(3)(q21q26.2)] or internal translocations in it—[t(3;3)(q21;q26.2);] RPN1/EVI1;<br>Megakaryoblastic AML with translocations between chromosome 1 and 22—[t(1;22)(p13;q13);] RBM15/MKL1;<br>AML with mutated NPM1<br>AML with mutated CEBPA |
| AML with myelodysplasia-related changes | Includes people who have had a prior documented myelodysplastic syndrome (MDS) or myeloproliferative disease (MPD) that then has transformed into AML, or who have cytogenetic abnormalities characteristic for this type of AML (with previous history of MDS or MPD that has gone unnoticed in the past, but the cytogenetics is still suggestive of MDS/MPD history). This category of AML occurs most often in elderly people and often has a worse prognosis. Includes:<br>AML with complex karyotype<br>Unbalanced abnormalities<br>  AML with deletions of chromosome 7—[del(7q);]<br>  AML with deletions of chromosome 5—[del(5q);]<br>  AML with unbalanced chromosomal aberrations in chromosome 17—[i(17q)/t(17p);]<br>  AML with deletions of chromosome 13—[del(13q);]<br>  AML with deletions of chromosome 11—[del(11q);]<br>  AML with unbalanced chromosomal aberrations in chromosome 12—[del(12p)/t(12p);]<br>  AML with deletions of chromosome 9—[del(9q);]<br>  AML with aberrations in chromosome X—[idic(X)(q13);]<br>Balanced abnormalities<br>  AML with translocations between chromosome 11 and 16—[t(11;16)(q23;q13.3);], unrelated to previous chemotherapy or ionizing radiation<br>  AML with translocations between chromosome 3 and 21—[t(3;21)(q26.2;q22.1);], unrelated to previous chemotherapy or ionizing radiation<br>  AML with translocations between chromosome 1 and 3—[t(1;3)(p36.3;q21.1);]<br>  AML with translocations between chromosome 2 and 11—[t(2;11)(p21;q23);], unrelated to previous chemotherapy or ionizing radiation<br>  AML with translocations between chromosome 5 and 12—[t(5;12)(q33;p12);]<br>  AML with translocations between chromosome 5 and 7—[t(5;7)(q33;q11.2);]<br>  AML with translocations between chromosome 5 and 17—[t(5;17)(q33;p13);]<br>  AML with translocations between chromosome 5 and 10—[t(5;10)(q33;q21);]<br>  AML with translocations between chromosome 3 and 5—[t(3;5)(q25;q34);] |
| Therapy-related myeloid neoplasms | Includes people who have had prior chemotherapy and/or radiation and subsequently develop AML or MDS. These leukemias may be characterized by specific chromosomal abnormalities, and often carry a worse prognosis. |
| Myeloid sarcoma | Includes myeloid sarcoma. |
| Myeloid proliferations related to Down syndrome | Includes so-called "transient abnormal myelopoiesis" and "Myeloid leukemia associated with Down syndrome" |
| Blastic plasmacytoid dendritic cell neoplasm | Includes so-called "blastic plasmacytoid dendritic cell neoplasm" |
| AML not otherwise categorized | Includes subtypes of AML that do not fall into the above categories<br>  AML with minimal differentiation<br>  AML without maturation<br>  AML with maturation<br>  Acute myelomonocytic leukemia<br>  Acute monoblastic and monocytic leukemia<br>  Acute erythroid leukemia<br>  Acute megakaryoblastic leukemia<br>  Acute basophilic leukemia<br>  Acute panmyelosis with myelofibrosis |

An alternative classification scheme for AML is the French-American-British (FAB) classification system. The FAB classification system includes the subtypes of AML provided in Table 2 and is described in Bennett J M, et al. (August 1976). "Proposals for the classification of the acute leukemias. French-American-British (FAB) co-operative group" Br. J. Haematol. 33 (4): 451-8, doi: 10.1111/j.1365-2141.1976.tb03563.x. PMID 188440; and Bennett J M, et al. (June 1989) "Proposals for the classification of chronic (mature) B and T lymphoid leukemias. French-American-British (FAB) Cooperative Group" J. Clin. Pathol. 42 (6): 567-84, doi: 10.1136/jcp.42.6.567, PMC 1141984, PMID 2738163, the contents of each of which are incorporated herein by reference.

TABLE 2

| Type | Name | Cytogenetics |
|---|---|---|
| M0 | acute myeloblastic leukemia, minimally differentiated | |
| M1 | acute myeloblastic leukemia, without maturation | |
| M2 | acute myeloblastic leukemia, with granulocytic maturation | t(8;21)(q22;q22), t(6;9) |
| M3 | promyelocytic, or acute promyelocytic leukemia (APL) | t(15;17) |

TABLE 2-continued

| Type | Name | Cytogenetics |
|---|---|---|
| M4 | acute myelomonocytic leukemia | inv(16)(p13q22), del(16q) |
| M4eo | myelomonocytic together with bone marrow eosinophilia | inv(16), t(16;16) |
| M5 | acute monoblastic leukemia (M5a) or acute monocytic leukemia (M5b) | del (11q), t(9;11), t(11;19) |
| M6 | acute erythroid leukemias, including erythroleukemia (M6a) and very rare pure erythroid leukemia (M6b) | |
| M7 | acute megakaryoblastic leukemia | t(1;22) |

The condition may be an inflammatory or autoimmune disorder. For example and without limitation, the inflammatory or autoimmune disorder may be arthritis, hepatitis, chronic obstructive pulmonary disease, multiple sclerosis, or tendonitis.

The condition may be a psychiatric disorder. For example and without limitation, the psychiatric disorder may be anxiety, stress, obsessive-compulsive disorder, depression, panic disorder, psychosis, addiction, alcoholism, attention deficit hyperactivity, agoraphobia, schizophrenia, or social phobia.

The condition may be an infection. The infection may be a viral infection. For example and without limitation, the virus infection may be infection with an adenovirus, coronavirus, enterovirus, human metapneumovirus, human parainfluenza virus, human respiratory syncytial virus, influenza virus, or rhinovirus. The coronavirus may be Middle East respiratory syndrome coronavirus (MERS-COV), severe acute respiratory syndrome coronavirus (SARS-COV), or severe acute respiratory syndrome coronavirus 2 (SARS-COV-2). The influenza virus may be influenza A, influenza B, influenza C, or influenza D. The influenza A virus may be a H1N1, H3N2, N9N2, or H5N1 strain.

The infection may affect a particular tissue, organ, or system. The infection may affect one or more of the alveoli, bronchi, bronchioles, larynx, lungs, nasal cavities, nose, pharynx, respiratory system, sinuses, and trachea.

The condition may include a genetic mutation such as MYC amplification or PTEN loss that leads to increased dependence on the metabolic pathway, such as increased "addiction" to glutamine.

The condition may include or affect a sub-population of patients. For example, the patients may be pediatric, newborn, neonates, infants, children, adolescent, pre-teens, teenagers, adults, or elderly. The patients may be in critical care, intensive care, neonatal intensive care, pediatric intensive care, coronary care, cardiothoracic care, surgical intensive care, medical intensive care, long-term intensive care, an operating room, an ambulance, a field hospital, or an out-of-hospital field setting.

Monitoring the Level of a Metabolite in a Sample

Methods of treating a condition in a subject may include monitoring the level of a metabolite, such as DHO, in a sample obtained from the subject. Monitoring the level of a metabolite may include receiving information about the measured level of the metabolite. Monitoring the level of a metabolite may include measuring the metabolite.

In some embodiments, the metabolite is measured by mass spectrometry, optionally in combination with liquid chromatography. Molecules may be ionized for mass spectrometry by any method known in the art, such as ambient ionization, chemical ionization (CI), desorption electrospray ionization (DESI), electron impact (EI), electrospray ionization (ESI), fast-atom bombardment (FAB), field ionization, laser ionization (LIMS), matrix-assisted laser desorption ionization (MALDI), paper spray ionization, plasma and glow discharge, plasma-desorption ionization (PD), resonance ionization (RIMS), secondary ionization (SIMS), spark source, or thermal ionization (TIMS). Methods of mass spectrometry are known in the art and described in, for example, U.S. Pat. Nos. 8,895,918; 9,546,979; 9,761,426; Hoffman and Stroobant, Mass Spectrometry: Principles and Applications (2nd ed.). John Wiley and Sons (2001), ISBN 0-471-48566-7; Dass, Principles and practice of biological mass spectrometry, New York: John Wiley (2001) ISBN 0-471-33053-1; and Lee, ed., Mass Spectrometry Handbook, John Wiley and Sons, (2012) ISBN: 978-0-470-53673-5, the contents of each of which are incorporated herein by reference.

In certain embodiments, a sample can be directly ionized without the need for use of a separation system. In other embodiments, mass spectrometry is performed in conjunction with a method for resolving and identifying ionic species. Suitable methods include chromatography, capillary electrophoresis-mass spectrometry, and ion mobility. Chromatographic methods include gas chromatography, liquid chromatography (LC), high-pressure liquid chromatography (HPLC), hydrophilic interaction chromatography (HILIC), ultra-performance liquid chromatography (UPLC), and reversed-phase liquid chromatography (RPLC). In a preferred embodiment, liquid chromatography-mass spectrometry (LC-MS) is used. Methods of coupling chromatography and mass spectrometry are known in the art and described in, for example, Holcapek and Brydwell, eds. Handbook of Advanced Chromatography/Mass Spectrometry Techniques, Academic Press and AOCS Press (2017), ISBN 9780128117323; Pitt, Principles and Applications of Liquid Chromatography-Mass Spectrometry in Clinical Biochemistry, The Clinical Biochemist Reviews. 30(1): 19-34 (2017) ISSN 0159-8090; Niessen, Liquid Chromatography-Mass Spectrometry, Third Edition. Boca Raton: CRC Taylor & Francis. pp. 50-90. (2006) ISBN 9780824740825; Ohnesorge et al., Quantitation in capillary electrophoresis-mass spectrometry, Electrophoresis. 26 (21): 3973-87 (2005) doi: 10.1002/elps.200500398; Kolch et al., Capillary electrophoresis-mass spectrometry as a powerful tool in clinical diagnosis and biomarker discovery, Mass Spectrom Rev. 24 (6): 959-77. (2005) doi: 10.1002/mas.20051; Kanu et al., Ion mobility-mass spectrometry, Journal of Mass Spectrometry, 43 (1): 1-22 (2008) doi: 10.1002/jms.1383, the contents of which are incorporated herein by reference.

A sample may be obtained from any organ or tissue in the individual to be tested, provided that the sample is obtained in a liquid form or can be pre-treated to take a liquid form. For example and without limitation, the sample may be a blood sample, a urine sample, a serum sample, a semen sample, a sputum sample, a lymphatic fluid sample, a cerebrospinal fluid sample, a plasma sample, a pus sample, an amniotic fluid sample, a bodily fluid sample, a stool sample, a biopsy sample, a needle aspiration biopsy sample, a swab sample, a mouthwash sample, a cancer sample, a tumor sample, a tissue sample, a cell sample, a synovial fluid sample, a phlegm sample, a saliva sample, a sweat sample, or a combination of such samples. The sample may also be a solid or semi-solid sample, such as a tissue sample, feces sample, or stool sample, that has been treated to take a liquid form by, for example, homogenization, sonication, pipette trituration, cell lysis etc. For the methods described herein, it is preferred that a sample is from plasma, serum, whole blood, or sputum.

The sample may be kept in a temperature-controlled environment to preserve the stability of the metabolite. For example, DHO is more stable at lower temperatures, and the increased stability facilitates analysis of this metabolite from samples. Thus, samples may be stored at 4° C., −20° C., or −80° C.

In some embodiments, a sample is treated to remove cells or other biological particulates. Methods for removing cells from a blood or other sample are well known in the art and may include e.g., centrifugation, sedimentation, ultrafiltration, immune selection, etc.

The sample may be obtained from an individual before or after administration to the subject of an agent that alters activity of a metabolic pathway, such as inhibitor of an enzyme in the pathway. For example, the sample may be obtained 1 hour, 2 hours, 4 hours, 6 hours, 8 hours, 12 hours, 24 hours, 36 hours, 2 days, 3 days, 4 days, 5 days, 6 days, 7 days or more before administration of an agent, or it may be obtained 1 hour, 2 hours, 4 hours, 6 hours, 8 hours, 12 hours, 24 hours, 36 hours, 2 days, 3 days, 4 days, 5 days, 6 days, 7 days or more after administration of an agent.

Dosing Regimens, Including Determining Dosing Regimens Based on Levels of a Metabolite Methods of treating a condition may include providing to the subject a composition containing polymorphic form C of brequinar sodium salt according to a dosing regimen. Compositions containing polymorphic form C of brequinar sodium salt in a solid form may be administered in their solid form, or they may be mixed, dissolved, or converted to another format prior to administration. Such composition may be provided orally, intravenously, enterally, parenterally, dermally, buccally, topically, transdermally, by injection, subcutaneously, nasally, pulmonarily, or with or on an implantable medical device.

A dosing regimen may include a dosage and a schedule of administration. A dosage of brequinar includes an amount of the drug. The amount of brequinar may be expressed in absolute terms, e.g., mass of brequinar. The amount of brequinar may be expressed in terms relating the amount to the subject, e.g., brequinar mass per subject mass, or brequinar mass per subject volume. The amount of brequinar may be expressed in terms that indicate an effect of the drug, e.g., amount of brequinar that achieves a target concentration in a tissue or sample from the subject. A dosage may include a period of time over which the amount is to be administered to the subject. Thus, the dosage may include an amount of brequinar per unit of time. The dosage may include a single dose, i.e., the entire amount may be provided at once. Alternatively, the dosage may include multiple, e.g., 2, 3, 4, 6, or 8, doses that collectively achieve the entire amount of the dosage. A schedule of administration may be described by the interval between doses, e.g., every 24 hours, every 48 hours, etc., or by the number doses administered during a given period, e.g., once per week, twice per week, etc.

The dosing regimen may include a schedule for administration of doses. For example, doses may be administered at regular intervals, such as every 24 hours, every 36 hours, every 48 hours, every 60 hours, every 72 hours, every 84 hours, every 96 hours, every 5 days, every 6 days, every week, every 2 weeks, every 3 weeks, or every 4 weeks. Alternatively, doses may be administered according to a schedule that does not require precisely regular intervals. For example, doses may be administered once per week, twice per week, three times per week, four times per week, once per month, twice per month, three times per month, four times per month, five times per month, or six times per month.

For example and without limitation, the dosage of brequinar may be from about 10 mg to about 180 mg, from about 26 mg to about 180 mg, from about 51 mg to about 180 mg, from about 76 mg to about 180 mg, from about 101 mg to about 180 mg, from about 126 mg to about 180 mg, from about 151 mg to about 180 mg, from about 10 mg to about 150 mg, from about 26 mg to about 150 mg, from about 51 mg to about 150 mg, from about 76 mg to about 150 mg, from about 101 mg to about 150 mg, from about 126 mg to about 150 mg, from about 10 mg to about 125 mg, from about 26 mg to about 125 mg, from about 51 mg to about 125 mg, from about 76 mg to about 125 mg, from about 101 mg to about 125 mg, from about 10 mg to about 100 mg, from about 26 mg to about 100 mg, from about 51 mg to about 100 mg, from about 76 mg to about 100 mg, from about 10 mg to about 75 mg, from about 26 mg to about 75 mg, from about 51 mg to about 75 mg, from about 10 mg to about 50 mg, from about 26 mg to about 50 mg, about 10 mg, about 25 mg, about 50 mg, about 75 mg, about 100 mg, about 125 mg, about 150 mg, or about 180 mg.

For example and without limitation, the dosage of brequinar may be from about 10 mg to about 4000 mg, from about 26 mg to about 4000 mg, from about 51 mg to about 4000 mg, from about 76 mg to about 4000 mg, from about 101 mg to about 4000 mg, from about 151 mg to about 4000 mg, from about 201 mg to about 4000 mg, from about 10 mg to about 2000 mg, from about 26 mg to about 2000 mg, from about 51 mg to about 2000 mg, from about 76 mg to about 2000 mg, from about 101 mg to about 2000 mg, from about 151 mg to about 2000 mg, from about 201 mg to about 2000 mg, from about 10 mg to about 1000 mg, from about 26 mg to about 1000 mg, from about 51 mg to about 1000 mg, from about 76 mg to about 1000 mg, from about 101 mg to about 1000 mg, from about 151 mg to about 1000 mg, from about 201 mg to about 1000 mg, from about 10 mg to about 500 mg, from about 26 mg to about 500 mg, from about 51 mg to about 500 mg, from about 76 mg to about 500 mg, from about 101 mg to about 500 mg, from about 151 mg to about 500 mg, from about 201 mg to about 500 mg, from about 10 mg to about 300 mg, from about 26 mg to about 300 mg, from about 51 mg to about 300 mg, from about 76 mg to about 300 mg, from about 101 mg to about 300 mg, from about 151 mg to about 300 mg, from about 201 mg to about 300 mg, from about 10 mg to about 200 mg, from about 26 mg to about 200 mg, from about 51 mg to about 200 mg, from about 76 mg to about 200 mg, from about 101 mg to about 200 mg, from about 151 mg to about 200 mg, from about 10 mg to about 150 mg, from about 26 mg to about 150 mg, from about 51 mg to about 150 mg, from about 76 mg to about 150 mg, from about 101 mg to about 150 mg, from about 10 mg to about 100 mg, from about 26 mg to about 100 mg, from about 51 mg to about 100 mg, from about 76 mg to about 100 mg, about 50 mg, about 75 mg, about 100 mg, about 200 mg, about 250 mg, about 300 mg, about 400 mg, about 500 mg, about 1000 mg, about 2000 mg, or about 4000 mg.

For example and without limitation, a dosing regimen for administration of brequinar, e.g., brequinar sodium, to a human subject may be as follows: 100 mg/m$^2$, administered orally twice weekly; 125 mg/m$^2$, administered orally twice weekly; 150 mg/m$^2$, administered orally twice weekly; 200 mg/m$^2$, administered orally twice weekly; 250 mg/m$^2$, administered orally twice weekly; 275 mg/m$^2$, administered orally twice weekly; 300 mg/m$^2$, administered orally twice weekly; 350 mg/m$^2$, administered orally twice weekly; 400 mg/m$^2$, administered orally twice weekly; 425 mg/m$^2$, administered orally twice weekly; 450 mg/m$^2$, administered orally twice weekly; 500 mg/m$^2$, administered orally twice weekly; 550 mg/m$^2$, administered orally twice weekly; 600 mg/m$^2$, administered orally twice weekly; 650 mg/m$^2$, administered orally twice weekly; 700 mg/m$^2$, administered orally twice weekly; 750 mg/m$^2$, administered orally twice weekly; 800 mg/m$^2$, administered orally twice weekly; 100 mg/m$^2$, administered orally every 72 hours; 125 mg/m$^2$, administered orally every 72 hours; 150 mg/m$^2$, administered orally every 72 hours; 200 mg/m$^2$, administered orally every 72 hours; 250 mg/m$^2$, administered orally every 72 hours; 275 mg/m$^2$, administered orally every 72 hours; 300 mg/m$^2$, administered orally every 72 hours; 350 mg/m$^2$, administered orally every 72 hours; 400 mg/m$^2$, administered orally every 72 hours; 425 mg/m$^2$, administered orally every 72 hours; 450 mg/m$^2$, administered orally every 72 hours; 500 mg/m$^2$, administered orally every 72 hours; 550 mg/m$^2$, administered orally every 72 hours; 600 mg/m$^2$, administered orally every 72 hours; 650 mg/m$^2$, administered orally every 72 hours; 700 mg/m$^2$, administered orally every 72 hours; 750 mg/m$^2$, administered orally every 72 hours; 800 mg/m$^2$, administered orally every 72 hours; 100 mg/m$^2$, administered orally every 84 hours; 125 mg/m$^2$, administered orally every 84 hours; 150 mg/m$^2$, administered orally every 84 hours; 200 mg/m$^2$, administered orally every 84 hours; 250 mg/m$^2$, administered orally every 84 hours; 275 mg/m$^2$, administered orally every 84 hours; 300 mg/m$^2$, administered orally every 84 hours; 350 mg/m$^2$, administered orally every 84 hours; 400 mg/m$^2$, administered orally every 84 hours; 425 mg/m$^2$, administered orally every 84 hours; 450 mg/m$^2$, administered orally every 84 hours; 500 mg/m$^2$, administered orally every 84 hours; 550 mg/m$^2$, administered orally every 84 hours; 600 mg/m$^2$, administered orally every 84 hours; 650 mg/m$^2$, administered orally every 84 hours; 700 mg/m$^2$, administered orally every 84 hours; 750 mg/m$^2$, administered orally every 84 hours; 800 mg/m$^2$, administered orally every 84 hours; 100 mg/m$^2$, administered orally every 96 hours; 125 mg/m$^2$, administered orally every 96 hours; 150 mg/m$^2$, administered orally every 96 hours; 200 mg/m$^2$, administered orally every 96 hours; 250 mg/m$^2$, administered orally every 96 hours; 275 mg/m$^2$, administered orally every 96 hours; 300 mg/m$^2$, administered orally every 96 hours; 350 mg/m$^2$, administered orally every 96 hours; 400 mg/m$^2$, administered orally every 96 hours; 425 mg/m$^2$, administered orally every 96 hours; 450 mg/m$^2$, administered orally every 96 hours; 500 mg/m$^2$, administered orally every 96 hours; 550 mg/m$^2$, administered orally every 96 hours; 600 mg/m$^2$, administered orally every 96 hours; 650 mg/m$^2$, administered orally every 96 hours; 700 mg/m$^2$, administered orally every 96 hours; 750 mg/m$^2$, administered orally every 96 hours; or 800 mg/m$^2$, administered orally every 96 hours.

For example and without limitation, the dosage of brequinar may be an amount sufficient to maintain a concentration of brequinar in a lung of the subject of at least 0.01 μg/mL, at least 0.03 μg/mL, at least 0.1 μg/mL, at least 0.2 μg/mL, at least 0.3 μg/mL, at least 0.375 μg/mL, at least 0.4 μg/mL, at least 0.5 μg/mL, at least 0.6 μg/mL, at least 0.8 μg/mL, at least 1 μg/mL, at least 1.5 μg/mL, or at least 2 μg/mL for a 24-hour period.

A dosing regimen may contain a single dosage. Alternatively, a dosing regimen may contain multiple dosages. For example, a dosing regimen may include 1, 2, 3, 4, 5, 6, 7, 8, 9, 10, 11, 12, 13, 14, 15, or more dosages. A dosing regimen may include multiple dosages provided consecutively. For example, a dosage may include a defined amount of brequinar provided over a defined period, e.g., one day or 24 hours, and the dosing regimen may include dosages provided in two or more consecutive periods, e.g., days or 24-hour periods.

In dosing regimens that include multiple dosages, each dosage may be the same, i.e., each includes the same amount of brequinar. Alternatively, dosing regimens may include dosages that are not all the same. In some embodiments, the dosing regimen includes multiple consecutive dosages in which the first one, two, three, or four dosages are higher than subsequent dosages. In some embodiments, the dosing regimen includes multiple consecutive dosages in which the first the first one, two, three, or four dosages are lower than subsequent dosages. In the aforementioned embodiments, the subsequent dosages may all the same, or they may differ from each other as well. A variety of other dosage variations are possible within the scope of the invention. For example and without limitation, the dosing regimen may include any of the following sequences of dosages: alternation between high and low dosages; stepwise decreases or increases in individual dosages; stepwise decreases or increases in which one or more steps include two or more dosages that are the same; and patterns in which one or more of the aforementioned sequences is repeated or interspersed another aforementioned sequence. Each dosage may independently be selected from any of the dosages described above. For example, the first dosage may be 100 mg, and the subsequent dosages may be 25 mg. 50 mg, or 75 mg.

The dosing regimen may include a dosage-free period in which the subject does not receive brequinar or a pharmaceutically acceptable salt thereof. The dosage-free period may be at least 12 hours, at least 24 hours, at least 36 hours, at least 48 hours, at least 60 hours, at least 72 hours, at least 5 days, at least 7 days, at least 10 days, at least 14 days, about 12 hours, about 24 hours, about 36 hours, about 48 hours, about 60 hours, about 72 hours, about 5 days, about 7 days, about 10 days, or about 14 days.

The dosage-free period may follow a dosage. The dosage-free period may follow multiple dosages provided over consecutive 24-hour periods. The dosage-free period may follow multiple dosages provided over 2, 3, 4, 5, 6, 7, 8, 9, 10, 11, 12, 13, 14, or 15 consecutive 24-hour periods.

The method may include determining a dosing regimen for a subject. The dosing regimen may be determined by comparing a measured level of a metabolite, e.g., DHO, in a sample obtained from a subject to a reference that provides an association between the measured level and a recommended dosage adjustment of brequinar. For example, the reference may provide a relationship between administration of the brequinar composition and levels of the metabolite in the subject. The relationship can be empirically determined from a known dose and time of administration of brequinar and measured levels of the metabolite at one or more subsequent time points. The reference may include a relationship between measured levels of brequinar or a metabolic product of brequinar and measured levels of the metabolite. Methods of dosing brequinar based on measured metabolite levels are known in the art and described in, for example, International Patent Publication Nos. WO 2019/191030 and WO 2019/191032, the contents of which are incorporated herein by reference.

From the comparison between the measured level of the metabolite and the reference, a dosing regimen may then be determined. The dosing regimen may include a dosage of brequinar, a time for administration of the dosage, or both. The dosing regimen may be determined de novo, or it may comprise an adjustment to a previous dosing regimen, such as an adjustment in the dosage, the interval between administration of dosages, or both.

The dosing regimen is designed to deliver brequinar to the subject in an amount that achieves a therapeutic effect. The therapeutic effect may be a sign or symptom of a disease, disorder, or condition. The therapeutic effect may be inhibition of DHODH, or it may be a change in an indicator of inhibition of DHODH. The indicator may be a metabolite, such as DHO, and the therapeutic effect may be an increase or decrease in levels of the metabolite. The therapeutic effect may be a decrease in number of cancer cells, a decrease in proliferation of cancer cells, an increase in differentiation of pre-cancerous cells, such as myeloblasts, complete remission of cancer, complete remission with incomplete hematologic recovery, morphologic leukemia-free stat, or partial remission. Increased differentiation of myeloblasts may be assessed by one or more of expression of CD14, expression of CD11b, nuclear morphology, and cytoplasmic granules.

The dosing regimen may ensure that levels of a metabolite, such as DHO, are raised or maintained at a minimum threshold required to achieve a certain effect. For example, the dosing regimen may raise or maintain levels of the metabolite above a threshold level in the subject for a certain time period. The time period may include a minimum, a maximum, or both. For example, the dosing regimen may raise or maintain levels of the metabolite above the threshold level for at least 6 hours, 12, hours, 24 hours, at least 48 hours, at least 60 hours, at least 72 hours, at least 84 hours, at least 96 hours, at least 5 days, at least 6 days, at least 7 days, at least 10 days, at least 2 weeks, or more. The dosing regimen may raise or maintain levels of the metabolite above the threshold level for not more than 24 hours, not more than 36 hours, not more than 48 hours, not more than 60 hours, not more than 72 hours, not more than 84 hours, not more than 96 hours, not more than 5 days, not more than 6 days, not more than 7 days, not more than 10 days, or not more than 2 weeks. The dosing regimen may raise or maintain levels of the metabolite above the threshold level for at least 72 hours but not more than 96 hours, for at least 72 hours but not more than 5 days, for at least 72 hours but not more than 6 days, for at least 72 hours but not more than 7 days, for at least 96 hours but not more than 7 days.

The dosing regimen may ensure that levels of a metabolite, such as DHO, do not exceed or are maintained below a maximum threshold that is associated with toxicity. Levels of the metabolite above a maximum threshold may indicate that brequinar is causing or is likely to cause an adverse event in the subject. For example and without limitation, adverse events include abdominal pain, anemia, anorexia, blood disorders, constipation, diarrhea, dyspepsia, fatigue, fever, granulocytopenia, headache, infection, leukopenia, mucositis, nausea, pain at the injection site, phlebitis, photosensitivity, rash, somnolence, stomatitis, thrombocytopenia, and vomiting.

The dosing regimen may include a time point for administration of one or more subsequent doses to raise or maintain levels of the metabolite, such as DHO, above a threshold level for a certain time period. The time point for administration of a subsequent dose may be relative to an earlier time point. For example, the time point for administration of a subsequent dose may be relative to a time point when a previous dose was administered or a time point when a sample was obtained from a subject.

The dosing regimen may include a schedule for administration of doses. For example, doses may be administered at regular intervals, such as every 24 hours, every 36 hours, every 48 hours, every 60 hours, every 72 hours, every 84 hours, every 96 hours, every 5 days, every 6 days, every week, every 2 weeks, every 3 weeks, or every 4 weeks. Alternatively, doses may be administered according to a schedule that does not require precisely regular intervals. For example, doses may be administered once per week, twice per week, three times per week, four times per week, once per month, twice per month, three times per month, four times per month, five times per month, or six times per month.

For example and without limitation, a dosing regimen for administration of brequinar, e.g., brequinar sodium, to a human subject may be as follows: 100 mg/m$^2$, administered intravenously twice weekly; 125 mg/m$^2$, administered intravenously twice weekly; 150 mg/m$^2$, administered intravenously twice weekly; 200 mg/m$^2$, administered intravenously twice weekly; 250 mg/m$^2$, administered intravenously twice weekly; 275 mg/m$^2$, administered intravenously twice weekly; 300 mg/m$^2$, administered intravenously twice weekly; 350 mg/m$^2$, administered intravenously twice weekly; 400 mg/m$^2$, administered intravenously twice weekly; 425 mg/m$^2$, administered intravenously twice weekly; 450 mg/m$^2$, administered intravenously twice weekly; 500 mg/m$^2$, administered intravenously twice weekly; 550 mg/m$^2$, administered intravenously twice weekly; 600 mg/m$^2$, administered intravenously twice weekly; 650 mg/m$^2$, administered intravenously twice weekly; 700 mg/m$^2$, administered intravenously twice weekly; 750 mg/m$^2$, administered intravenously twice weekly; 800 mg/m$^2$, administered intravenously twice weekly; 100 mg/m$^2$, administered intravenously every 72 hours; 125 mg/m$^2$, administered intravenously every 72 hours; 150 mg/m$^2$, administered intravenously every 72 hours; 200 mg/m$^2$, administered intravenously every 72 hours; 250 mg/m$^2$, administered intravenously every 72 hours; 275 mg/m$^2$, administered intravenously every 72 hours; 300 mg/m$^2$, administered intravenously every 72 hours; 350 mg/m$^2$, administered intravenously every 72 hours; 400 mg/m$^2$, administered intravenously every 72 hours; 425 mg/m$^2$, administered intravenously every 72 hours; 450 mg/m$^2$, administered intravenously every 72 hours; 500 mg/m$^2$, administered intravenously every 72 hours; 550 mg/m$^2$, administered intravenously every 72 hours; 600 mg/m$^2$, administered intravenously every 72 hours; 650 mg/m$^2$, administered intravenously every 72 hours; 700 mg/m$^2$, administered intravenously every 72 hours; 750 mg/m$^2$, administered intravenously every 72 hours; 800 mg/m$^2$, administered intravenously every 72 hours; 100 mg/m$^2$, administered intravenously every 84 hours; 125 mg/m$^2$, administered intravenously every 84 hours; 150 mg/m$^2$, administered intravenously every 84 hours; 200 mg/m$^2$, administered intravenously every 84 hours; 250 mg/m$^2$, administered intravenously every 84 hours; 275 mg/m$^2$, administered intravenously every 84 hours; 300 mg/m$^2$, administered intravenously every 84 hours; 350 mg/m$^2$, administered intravenously every 84 hours; 400 mg/m$^2$, administered intravenously every 84 hours; 425 mg/m$^2$, administered intravenously every 84 hours; 450 mg/m$^2$, administered intravenously every 84 hours; 500 mg/m$^2$, administered intravenously every 84 hours; 550 mg/m$^2$, administered intravenously every 84 hours; 600 mg/m$^2$, administered intravenously every 84 hours; 650 mg/m$^2$, administered intravenously every 84 hours; 700 mg/m$^2$, administered intravenously every 84 hours; 750 mg/m$^2$, administered intravenously every 84 hours; 800 mg/m$^2$, administered intravenously every 84 hours; 100 mg/m$^2$, administered intravenously every 96 hours; 125 mg/m², administered intravenously every 96 hours; 150 mg/m², administered intravenously every 96 hours; 200 mg/m², administered intravenously every 96 hours; 250 mg/m², administered intravenously every 96 hours; 275 mg/m², administered intravenously every 96 hours; 300 mg/m², administered intravenously every 96 hours; 350 mg/m², administered intravenously every 96 hours; 400 mg/m², administered intravenously every 96 hours; 425 mg/m², administered intravenously every 96 hours; 450 mg/m², administered intravenously every 96 hours; 500 mg/m², administered intravenously every 96 hours; 550 mg/m², administered intravenously every 96 hours; 600 mg/m², administered intravenously every 96 hours; 650 mg/m², administered intravenously every 96 hours; 700 mg/m², administered intravenously every 96 hours; 750 mg/m², administered intravenously every 96 hours; 800 mg/m², administered intravenously every 96 hours; 100 mg/m², administered orally twice weekly; 125 mg/m², administered orally twice weekly; 150 mg/m², administered orally twice weekly; 200 mg/m², administered orally twice weekly; 250 mg/m², administered orally twice weekly; 275 mg/m², administered orally twice weekly; 300 mg/m², administered orally twice weekly; 350 mg/m², administered orally twice weekly; 400 mg/m², administered orally twice weekly; 425 mg/m², administered orally twice weekly; 450 mg/m², administered orally twice weekly; 500 mg/m², administered orally twice weekly; 550 mg/m², administered orally twice weekly; 600 mg/m², administered orally twice weekly; 650 mg/m², administered orally twice weekly; 700 mg/m², administered orally twice weekly; 750 mg/m², administered orally twice weekly; 800 mg/m², administered orally twice weekly; 100 mg/m², administered orally every 72 hours; 125 mg/m², administered orally every 72 hours; 150 mg/m², administered orally every 72 hours; 200 mg/m², administered orally every 72 hours; 250 mg/m², administered orally every 72 hours; 275 mg/m², administered orally every 72 hours; 300 mg/m², administered orally every 72 hours; 350 mg/m², administered orally every 72 hours; 400 mg/m², administered orally every 72 hours; 425 mg/m², administered orally every 72 hours; 450 mg/m², administered orally every 72 hours; 500 mg/m², administered orally every 72 hours; 550 mg/m², administered orally every 72 hours; 600 mg/m², administered orally every 72 hours; 650 mg/m², administered orally every 72 hours; 700 mg/m², administered orally every 72 hours; 750 mg/m², administered orally every 72 hours; 800 mg/m², administered orally every 72 hours; 100 mg/m², administered orally every 84 hours; 125 mg/m², administered orally every 84 hours; 150 mg/m², administered orally every 84 hours; 200 mg/m², administered orally every 84 hours; 250 mg/m², administered orally every 84 hours; 275 mg/m², administered orally every 84 hours; 300 mg/m², administered orally every 84 hours; 350 mg/m², administered orally every 84 hours; 400 mg/m², administered orally every 84 hours; 425 mg/m², administered orally every 84 hours; 450 mg/m², administered orally every 84 hours; 500 mg/m², administered orally every 84 hours; 550 mg/m², administered orally every 84 hours; 600 mg/m², administered orally every 84 hours; 650 mg/m², administered orally every 84 hours; 700 mg/m², administered orally every 84 hours; 750 mg/m², administered orally every 84 hours; 800 mg/m², administered orally every 84 hours; 100 mg/m², administered orally every 96 hours; 125 mg/m², administered orally every 96 hours; 150 mg/m², administered orally every 96 hours; 200 mg/m², administered orally every 96 hours; 250 mg/m², administered orally every 96 hours; 275 mg/m², administered orally every 96 hours; 300 mg/m², administered orally every 96 hours; 350 mg/m², administered orally every 96 hours; 400 mg/m², administered orally every 96 hours; 425 mg/m², administered orally every 96 hours; 450 mg/m², administered orally every 96 hours; 500 mg/m², administered orally every 96 hours; 550 mg/m², administered orally every 96 hours; 600 mg/m², administered orally every 96 hours; 650 mg/m², administered orally every 96 hours; 700 mg/m², administered orally every 96 hours; 750 mg/m², administered orally every 96 hours; or 800 mg/m², administered orally every 96 hours.

Minimum and maximum threshold levels of a metabolite depend on a variety of factors, such as the metabolites and type of sample. Minimum and maximum threshold levels may be expressed in absolute terms, e.g., in units of concentration, or in relative terms, e.g., in ratios relative to a baseline or reference value. For example, the minimum threshold (below which a patient may receive a dose increase or additional dose) could also be calculated in terms of increase from a pre-treatment DHO level or baseline level.

Minimum threshold levels of DHO or orotate in a human plasma sample may be about 0 ng/ml, about 10 ng/mL, about 20 ng/ml, about 50 ng/ml, about 100 ng/mL, about 150 ng/ml, about 200 ng/ml, about 250 ng/mL, about 300 ng/mL, about 350 ng/ml, about 400 ng/ml, about 450 ng/mL, about 500 ng/ml, about 550 ng/mL, about 600 ng/ml, about 650 ng/ml, about 700 ng/mL, about 750 ng/ml, about 800 ng/ml, about 850 ng/ml, about 900 ng/ml, about 950 ng/mL, about 1000 ng/ml, about 1250 ng/ml, about 1500 ng/ml, about 1750 ng/ml, about 2000 ng/ml, about 2500 ng/ml, about 3000 ng/ml, about 3500 ng/ml, about 4000 ng/ml, about 4500 ng/ml, about 5000 ng/ml, about 6000 ng/ml, about 8000 ng/ml, about 10,000 ng/ml, about 12,000 ng/ml, about 15,000 ng/ml, about 20,000 ng/ml, about 25,000 ng/ml, about 30,000 ng/ml, about 40,000 ng/ml, about 50,000 ng/ml, about 75,000 ng/ml, about 100,000 ng/ml, about 150,000 ng/ml, about 200,000 ng/ml, about 300,000 ng/ml, or about 400,000 ng/ml. The minimum threshold may include any value that falls between the values recited above. Thus, the minimum threshold may include any value between 0 ng/ml and 400,000 ng/ml.

Maximum threshold levels of DHO or orotate in a human plasma sample may be about 50 ng/mL, about 100 ng/mL, about 150 ng/mL, about 200 ng/ml, about 250 ng/ml, about 300 ng/mL, about 350 ng/mL, about 400 ng/mL, about 450 ng/mL, about 500 ng/ml, about 550 ng/mL, about 600 ng/mL, about 650 ng/mL, about 700 ng/mL, about 750 ng/ml, about 800 ng/mL, about 850 ng/ml, about 900 ng/ml, about 950 ng/ml, about 1000 ng/ml, about 1250 ng/ml, about 1500 ng/ml, about 1750 ng/ml, about 2000 ng/ml, about 2500 ng/ml, about 3000 ng/ml, about 3500 ng/ml, about 4000 ng/ml, about 4500 ng/ml, about 5000 ng/ml, about 6000 ng/ml, about 8000 ng/ml, about 10,000 ng/ml, about 12,000 ng/ml, about 15,000 ng/ml, about 20,000 ng/ml, about 25,000 ng/ml, about 30,000 ng/ml, about 40,000 ng/ml, about 50,000 ng/ml, about 75,000 ng/ml, about 100,000 ng/ml, about 150,000 ng/ml, about 200,000 ng/ml, about 300,000 ng/ml, about 400,000 ng/ml, or about 500,000 ng/ml. The maximum threshold may include any value that falls between the values recited above. Thus, the maximum threshold may include any value between 50 ng/ml and 500,000 ng/ml.

The minimum threshold of DHO or orotate may be about 1.5 times the baseline level, about 2 times the baseline level, about 2.5 times the baseline level, about 3 times the baseline level, about 4 times the baseline level, about 5 times the baseline level, about 10 times the baseline level, about 20 times the baseline level, about 50 times the baseline level, about 100 times the baseline level, about 200 times the baseline level, about 500 times the baseline level, about 1000 times the baseline level, about 2000 times the baseline level, or about 5000 times the baseline level. The minimum threshold may include any ratio that falls between those recited above. Thus, the minimum threshold may be any ratio between 1.5 times the baseline level and 5000 times the baseline level.

The maximum threshold of DHO or orotate may be about 2 times the baseline level, about 2.5 times the baseline level, about 3 times the baseline level, about 4 times the baseline level, about 5 times the baseline level, about 10 times the baseline level, about 20 times the baseline level, about 50 times the baseline level, about 100 times the baseline level, about 200 times the baseline level, about 500 times the baseline level, about 1000 times the baseline level, about 2000 times the baseline level, about 5000 times the baseline level, or about 10,000 times the baseline level. The maximum threshold may include any ratio that falls between those recited above. Thus, the maximum threshold may be any ratio between 2 times the baseline level and 10,000 times the baseline level.

Dosage of brequinar also depends on factors such as the type of subject and route of administration. The dosage may fall within a range for a given type of subject and route of administration, or the dosage may adjusted by a specified amount for a given type of subject and route of administration. For example, dosage of brequinar for oral or intravenous administration to a subject, such as human or mouse, may be about 1 mg/kg, about 2 mg/kg, about 5 mg/kg, about 7.5 mg/kg, about 10 mg/kg, about 15 mg/kg, about 20 mg/kg, about 25 mg/kg, about 50 mg/kg, about 75 mg/kg, or about 100 mg/kg. Dosage of brequinar for oral or intravenous administration to a subject, such as a human or mouse, may be adjusted by about 1 mg/kg, about 2 mg/kg, about 5 mg/kg, about 7.5 mg/kg, about 10 mg/kg, about 15 mg/kg, about 20 mg/kg, about 25 mg/kg, or about 50 mg/kg. Dosage of brequinar for oral or intravenous administration to an animal subject, such as a human or mouse, may be about 50 mg/m$^2$, about 100 mg/m$^2$, about 200 mg/m$^2$, about 300 mg/m$^2$, about 350 mg/m$^2$, about 400 mg/m$^2$, about 500 mg/m$^2$, about 600 mg/m$^2$, about 700 mg/m$^2$, about 750 mg/m$^2$, about 800 mg/m$^2$, or about 1000 mg/m$^2$. Dosage of brequinar for oral or intravenous administration to an animal subject, such as a human or mouse, may be adjusted by about 50 mg/m$^2$, about 100 mg/m$^2$, about 200 mg/m$^2$, about 300 mg/m$^2$, about 350 mg/m$^2$, or about 400 mg/m$^2$.

Methods may include determining whether the level of the metabolite is within a threshold range (e.g., above a minimal threshold and/or below a potential toxicity threshold) that warrants dosing, and/or that warrants dosing at a particular level or in a particular amount. Methods of determining the level of a metabolite and adjusting brequinar dosing regimen based on the determined levels of the metabolite are known in the art and described in, for example, International Patent Publication Nos. WO 2019/191030 and WO 2019/191032, the contents of which are incorporated herein by reference.

The methods may include providing at least one dose of brequinar to a subject whose plasma metabolite level has been determined and is below a pre-determined threshold (e.g., a pre-determined potential toxicity threshold and/or a pre-determined potential efficacy threshold). The predetermined threshold reflects percent inhibition of DHODH in the subject relative to a baseline determined for the subject. The baseline may be determined by an assay.

In order to maintain inhibition of DHODH at an effective threshold, multiple doses of brequinar may be administered to the subject. Dosing of brequinar may occur at different times and in different amounts. The present disclosure encompasses those methods that can maintain inhibition of the target enzyme at a consistent level at or above the efficacy threshold throughout the course of treatment. In some embodiments, the amount of inhibition of DHODH is measured by the amount of metabolite in the plasma of a subject.

The method may comprise a step of re-determining the subject's plasma metabolite level after administration of at least one dose. In some embodiments, the subject's plasma metabolite level is re-determined after each dose. The method may comprise administering at least one further dose of brequinar after the subject's plasma metabolite level has been determined again (e.g., after administering a first or previous dose) to be below the pre-determined threshold. If the subject's plasma metabolite level is determined to be above a pre-determined threshold, dosing can be discontinued. Thus, no further dose of brequinar is administered until the subject's plasma metabolite level has been determined to again be below a pre-determined threshold.

The methods may include administering brequinar to a subject at a dosage level at or near a cell-lethal level. Such dosage may be supplemented with a later dose at a reduced level, or by discontinuing of dosing. For example, the method may include administering a plurality of doses of brequinar according to a regimen characterized by at least first and second phases, wherein the first phase involves administration of at least one bolus dose of brequinar at a cell-lethal level, and the second phase involves either administration of at least one dose that is lower than the bolus dose or absence of administration of brequinar.

In some embodiments, brequinar is not administered during a second phase. In some embodiments, a second phase involves administration of uridine rescue therapy. In some embodiments, a bolus dose is or comprises a cell lethal dose. In some embodiments, a cell lethal dose is an amount of brequinar that is sufficient to cause apoptosis in normal (e.g., non-cancerous) cells in addition to target cells (e.g., cancer cells).

In some embodiments, the first phase and the second phase each comprise administering brequinar. In some embodiments, the first phase and the second phase are at different times. In some embodiments, the first phase and the second phase are on different days. In some embodiments, the first phase lasts for a period of time that is less than four days. In some embodiments, the first phase comprises administering brequinar, followed by a period of time in which no brequinar is administered. In some embodiments, the period of time in which no brequinar is administered is 3 to 7 days after the dose during the first phase. In some embodiments, the first phase comprises administering more than one dose.

In some embodiments, brequinar is administered during a second phase. In some embodiments, brequinar is administered sub-cell-lethal levels during the second phase. In some embodiments, the first phase is repeated after the second phase. In some embodiments, both the first and second phases are repeated.

In some embodiments, the present disclosure provides a method of administering brequinar to a subject in need thereof, according to a multi-phase protocol comprising a first phase in which at least one dose of brequinar is administered to the subject and a second phase in which at least one dose of brequinar is administered to the subject, wherein one or more doses administered in the second phase differs in amount and/or timing relative to other doses in its phase as compared with the dose(s) administered in the first phase.

In some embodiments, the level of a metabolite, e.g. DHO, is determined in a sample from the subject between the first and second phases. In some embodiments, the sample is a plasma sample. In some embodiments, the timing or amount of at least one dose administered after the metabolite level is determined or differs from that of at least one dose administered before the metabolite level was determined.

In some embodiments, the amount of brequinar that is administered to the patient is adjusted in view of the metabolite level in the subject's plasma. For example, in some embodiments, a first dose is administered in the first phase. In some embodiments, metabolite level is determined at a period of time after administration of the first dose.

In some embodiments, if the metabolite level is below a pre-determined level, the amount of brequinar administered in a second or subsequent dose is increased and/or the interval between doses is reduced. For example, in some such embodiments, the amount of brequinar administered may be increased, for example, by 100 mg/m$^2$. In some embodiments, the amount of brequinar administered in a second or subsequent dose is increased by 150 mg/m$^2$. In some embodiments, the amount of brequinar administered in a second or subsequent dose is increased by 200 mg/m$^2$. In some embodiments, the amount of brequinar administered may be increased by an adjustment amount determined based on change in metabolite levels observed between prior doses of different amounts administered to the subject.

In some embodiments, if the metabolite level is above a pre-determined level, the amount of brequinar administered in a second or subsequent dose is the same as the amount administered in the first or previous dose and/or the interval between doses is the same.

In some embodiments, if the metabolite level is above a pre-determined level, the amount of brequinar in a second or subsequent dose is decreased and/or the interval between doses is increased. For example, in some such embodiments, the amount of brequinar administered may be decreased, for example, by 50 mg/m$^2$. In some embodiments, if the metabolite level is above a pre-determined level, the amount of brequinar in a second or subsequent dose is decreased by 75 mg/m$^2$. In some embodiments, if the metabolite level is above a pre-determined level, the amount of brequinar in a second or subsequent dose is decreased by 100 mg/m$^2$. In some embodiments, the amount of brequinar administered may be decreased by an adjustment amount determined based on change in metabolite levels observed between prior doses of different amounts administered to the subject.

In some embodiments, the present disclosure provides a method of administering a later dose of brequinar to a patient who has previously received an earlier dose of brequinar, wherein the patient has had a level of metabolite assessed subsequent to administration of the earlier dose, and wherein the later dose is different than the earlier dose. The later dose may be different from the earlier dose in amount of brequinar included in the dose, time interval relative to an immediately prior or immediately subsequent dose, or combinations thereof. The amount of brequinar in the later dose may be less than that in the earlier dose.

The method may include administering multiple dose of brequinar, separated from one another by a time period that is longer than 2 days and shorter than 8 days. For example, the time period may be about 3 days.

In some embodiments, the metabolite level is determined in a sample from the subject before each dose is administered, and dosing is delayed or skipped if the determined metabolite level is above a pre-determined threshold. For example, the metabolite level may be determined about 12 hours, about 24 hours, about 36 hours, about 48 hours, about 60 hours, about 72 hours, about 84 hours, or about 96 hours after administration of brequinar.

The method may include administering brequinar according to a regimen approved in a trial in which a level of metabolite was measured in a patient between doses of brequinar. The regimen may include multiple doses whose amount and timing were determined in the trial to maintain the metabolite level within a range determined to indicate a degree of target enzyme inhibition below a toxic threshold and above a minimum threshold. The regimen may include determining the metabolite level in the subject after administration of one or more doses of brequinar.

In some embodiments, the regimen includes a dosing cycle in which an established pattern of doses is administered over a first period of time. In some embodiments, the regimen comprises a plurality of the dosing cycles. In some embodiments, the regimen includes a rest period during which brequinar is not administered between the cycles.

Combination Therapies

Methods of treating a condition in subject may entail the use of combination therapies that include a composition containing polymorphic form C of brequinar sodium salt and a second agent. Combination therapies may be used to treat any of the conditions described above, and the choice of second agent depends on the condition being treated.

For treatment of cancer, the second agent may target a signaling pathway. The second agent may target a mitogen-activated protein kinase pathway, AKT pathway, or phosphoinositide 3-kinase pathway. The second agent may target one or more effectors in a signaling pathway. The second agent may target a pathway that includes p38, enhancer of zeste 2 polycomb repressive complex 2 subunit (EZH2), E12/E47, epidermal growth factor receptor (EGFR), FOXC2, Hippo, kallikrein-related peptidase 6 (KLK6), neuropilin-2 (NRP2), polo-like kinase 1 (PLK1), polycomb group PcG (PRC2), Raf, sex determining region Y-box 2 (SOX2), SNAI1, SNAI2, transforming growth factor beta (TGF-β), TWIST1, and yes-associated protein 1 (YAP1), ZEB1, and/or ZEB2.

The second agent may be an inhibitor of p38. For example and without limitation, the p38 inhibitor may be AMG-548, asiatic acid, BIRB-796, BMS-582949, doramapimod, LY-2228820, pamapimod, PH-797804, SB-202190, SB-203580, SB-239063, SCIO-323, SCIO-469, SD-169, SKF-86002, TAK-715, VX-702, or VX-745. Other p38 inhibitors are described in, for example, U.S. Pat. Nos. 5,945,418; 6,093,742; 6,410,540; 6,509,363; 6,528,508; 6,617,324; 6,632,945; 6,635,644; 7,125,898; 7,135,575; 7,169,779; 7,423,047; 7,425,555; 7,521,447; 7,642,276; and 8,410,160; U.S Patent Publication No. 20020065296; and International Patent Publication No. WO 1999/032110.

For treatment of viral infections, the second agent may be an antiviral agent. The second agent may be a direct-acting antiviral agent, such as an agent that interferes with the function of a viral protein or enzyme. For example and without limitation, the antiviral agent may be a 3C-like main protease inhibitor, eIF4E inhibitor, helicase inhibitor, inhibitor of a viral structural protein, inhibitor of a virulence factor, inosine monophosphate dehydrogenase (IMPDH) inhibitor, interferon, papain-like proteinase inhibitor, protease inhibitor, or RNA-dependent RNA polymerase inhibitor. The cIF4E inhibitor may be ribavirin. The IMPDH inhibitor may be AS2643361, EICAR, FF-10501, mizoribine, mycophenolic acid, mycophenolate mofetil, ribavirin, selenazofurin, SM-108, taribavirin, tiazofurin, VX-148, VX-497, or VX-944. The interferon may be peginterferon alpha-2a or peginterferon alpha-2b. The protease inhibitor may be lopinavir, ritonavir, or a combination thereof. The RNA-dependent RNA polymerase inhibitor may be AT-511, AT-527, AT-9010, beclabuvir, dasabuvir, delcobuvir, favipiravir, filibuvir, radalbuvir, remdesivir, setrobuvir, or sofosbuvir. The virulence factor may be Nsp1. Nsp3c, or ORF7a.

The second agent may be an anti-inflammatory agent. Anti-inflammatory agents include corticosteroids and non-steroidal anti-inflammatory drugs (NSAIDs). For example and without limitation, anti-inflammatory agents include acematricin, acetate, aloe vera extracts, alpha-methyl dexamethasone, amcinafide, arnica flower, asprin, beclamethasone dipropionate, benorylate, benoxaprofen, betamethasone and its esters, chloroprednisone, chloroprednisone acetate, clescinolone, clidanac, clobetasol valerate, clocortelone, comfrey root, desonide, desoxycorticosterone acetate, desoxymethasone, dexamethasone, dexamethasone phosphate, dichlorisone, dichlorisone, diclofenac, di-florasone diacetate, diflucortolone and its derivatives, difluprednate, disalacid, enolic acids, extracts from genus Commiphom (*Commiphora Mukul*), extracts from genus Rubis (*Rubia Cordifolia*), fenamic acid derivatives, fenclofenac, fenugreek seed., fluadrenolone, flubiprofen, flucloronide, flucortine butyl ester, flucrolone acetonide, flufenamic acid derivatives such as N-(α,α,α-trifluoro-m-tolyl) anthranilic acid), flunisolide, fluocinonide, fluocortolone, fluorometha-lone, fluperolone, fluprednidine, fluprednisolone, flurandrenolone, furofenac, halcinonide, hydrocortamate, hydrocortisone, hydrocortisone acetate, hydrocortisone butyrate, hydrocortisone cyclopentylpropionate, hydrocortisone valerate, hydroxytriamcilone, indomethacin, isozepac, ketoprofen, matricarria flowers, meclofenamic acid derivatives (e.g. sodium meclofenamate), medrysone, mefenamic acid derivatives (e.g. N-(2,3-xyl-yl) anthranilic acid), meprednisone, methylprednisolone, naproxen, oxicams (e.g. piroxicam and isoxicam), oxyphenbutazone, paramethasone, phenylbutazone, prednisolone, prednisone, propionic acid esters such as ibuprofen, pyrazolidinediones, such as feprazone, safaprin, salicylic acid derivatives, sulfinpyrazone, sulindac, suprofen, tolmetin, triamcinolone acetonide, trimethasone, trisilate, willow bark, and zomepirac.

Combination therapies may include multiple periods in which different agents or different combinations of agents are provided to the subject. Different agents or different combinations of agents may be provided concurrently, sequentially, in overlapping periods, in temporally separated periods, or in any other manner known to one of ordinary skill in the art. Exemplary temporal regimens for administering combination therapies are provided below.

For example and without limitation, and combination therapy may include a first period and a second period that follows the first period, the periods being as follows: a first period during which a first agent but not a second agent is provided to the subject and a second period during which the second agent but not the first agent is provided to the subject; a first period during which a first agent and a second agent are provided to the subject and a second period during which the second agent but not the first agent is provided to the subject; a first period during which a first agent but not a second agent is provided to the subject and a second period during which the first agent and the second agent are provided to the subject; and a first period during which first combination of agents is provided to the subject and a second period during which a second, different combination of agents is provided to the subject. In particular embodiments, brequinar or a pharmaceutically acceptable salt thereof is provided to the subject during a first period, and an anti-inflammatory agent is provided to the subject during a second period that follows the first period. Brequinar or a pharmaceutically acceptable salt thereof may be withheld from the subject during the second period. The anti-inflammatory may or may not be provided during the first period. Brequinar or a pharmaceutically acceptable salt thereof may be provided during the first period according to a dosing regimen, such as any of those described above. In combination therapies, different therapeutic agents may be provided in a single formulation. For example, a combination therapy may include providing brequinar or a pharmaceutically acceptable salt thereof in the same formulation as a second agent, such as an antiviral agent or anti-inflammatory agent. In some embodiments, brequinar or a pharmaceutically acceptable salt thereof and dexamethasone are provided in the same formulation.

Alternatively, in combination therapies, different therapeutic agents may be provided in separate formulations. For example, a combination therapy may include providing brequinar or a pharmaceutically acceptable salt thereof and a second agent, such as an antiviral agent or anti-inflammatory agent, in separate formulations. In some embodiments, brequinar or a pharmaceutically acceptable salt thereof and dexamethasone are provided in separate formulations.

EXAMPLES

Example 1

Extensive research was conducted to discover a crystalline form of brequinar (BRQ) that would be a suitable pharmaceutical form for commercial oral manufacture. Earlier methods of BRQ production provide brequinar as a lyophilized powder that is suitable for intravenous administration when dissolved in an aqueous medium, but such methods do not produce a crystalline form suitable for commercial manufacture of capsules or tablets.

The polymorphic behaviors of BRQ were investigated to identify the optimal polymorph for further development. The polymorph screening and selection was performed with a typical manufacturing research batch of brequinar sodium salt called Pattern A (research batch: PS04375-1-E-P4). Polymorphic behaviors of this salt were investigated by equilibration at 25° C. and 50° C. experiments, equilibration under temperature cycling experiments, crystallization by fast and slow cooling experiments, crystallization by slow evaporation experiments, crystallization by anti-solvent addition experiments and crystallization by using vapor diffusion experiments.

FIG. 1 is an X-ray powder diffraction (XRPD) pattern of brequinar sodium salt from batch PS04375-1-E-P4.

FIG. 2 is a differential scanning calorimetry (DSC) thermogram of brequinar sodium salt from batch PS04375-1-E-P4.

FIG. 3 is a thermogravimetric analysis (TGA) thermogram of brequinar sodium salt from batch PS04375-1-E-P4.

The above results show that research batch brequinar sodium salt, called Pattern A, is polymorphic. Ten hydrates have been identified: Patterns A, B, C, D, E, F, G, H, I and J.

FIG. 4 is an overlay of XRPD scans Patterns A-J of brequinar sodium salt from batch PS04375-1-E-P4.

The polymorphic forms of brequinar are summarized in Table 3.

TABLE 3

| Polymorph | Crystallinity/ XRPD | Melting point/DSC Weight loss/TGA | Comments |
|---|---|---|---|
| Pattern A | high | Multiple peaks, 5.0% at 175° C. | Raw material, hydrate |
| Pattern B | high | Multiple peaks, 1.96% at 169° C. | hydrate KF 4.8% unstable, convert to Pattern C after 4 days at ambient condition. |
| Pattern C | high | Multiple peaks, 6.58% at 182° C. | hydrate KF 6.9% |
| Pattern D | high | Multiple peaks, 2.19% at 70° C., 3.54% at 145° C. | (EA 2% by ¹HNMR, KF 7.8%), convert to Pattern C after 3 days at ambient condition. |
| Pattern E | high | Multiple peaks, 2.44% at 60° C., 7.98% at 151° C. | Maybe solvate (ACN 6.5% by ¹HNMR, KF 8.8%), 2, unstable, convert to Pattern C after 1 week (closed cap storage). |
| Pattern F | high | Multiple peaks, 0.88% at 62° C., 7.63% at 131° C. | Maybe solvate (ACN 6.5% by ¹HNMR, KF 7.2%), 6, unstable, convert to Pattern C after 1 week (closed cap storage). |
| Pattern G | high | Multiple peaks, 10.41% at 75° C., 6.44% at 128° C. | Maybe solvate (Acetone 5.9% by ¹HNMR, KF 15.3%), unstable, convert to Pattern C after 2 weeks at ambient condition. |
| Pattern H | high | Multiple peaks, 10.57% at 72° C., 3.86% at 128° C. | Hydrate, Acetone 2.3% by ¹HNMR, KF 21.5% |
| Pattern I | high | Multiple peaks, 1.74% at 85° C., 4.21% at 184° C. | Acetone 0.1% by ¹HNMR, KF 7.3%, unstable, converts to Pattern C after 2 days at ambient condition. |
| Pattern J | high | Not carried | Unstable, convert to Pattern C after 2 weeks (closed cap storage). Error! Reference source not found. |

Of the polymorphic forms of brequinar sodium salt, Patterns B, D, E, F, G, I and J are unstable and convert into Pattern C under ambient condition. Pattern A, the starting material, is also a metastable form, and changes into different polymorphs occurred during polymorphic screening study. Pattern C remains the same under vacuum drying condition of 50° ° C. for 18 h. The data provided here demonstrated that Pattern C is a desired form for commercial development due to its stability during manufacturing and storage.

Figure 5:
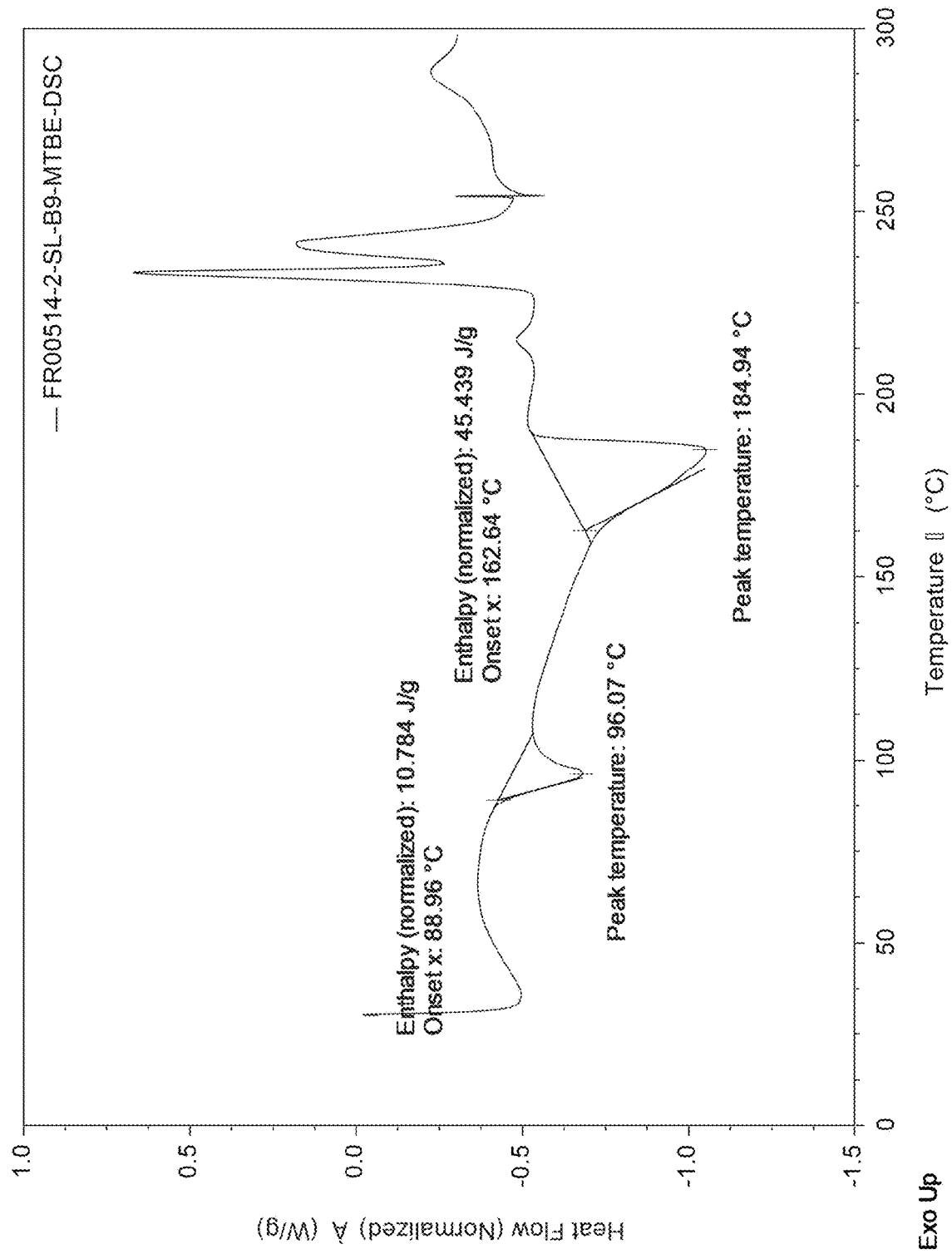
FIG. 5 is a DSC thermogram of polymorphic form C of brequinar sodium salt from batch FR00514-2-SL-B9.

FIG. 5 is a DSC thermogram of polymorphic form C of brequinar sodium salt from batch FR00514-2-SL-B9.

Figure 6:
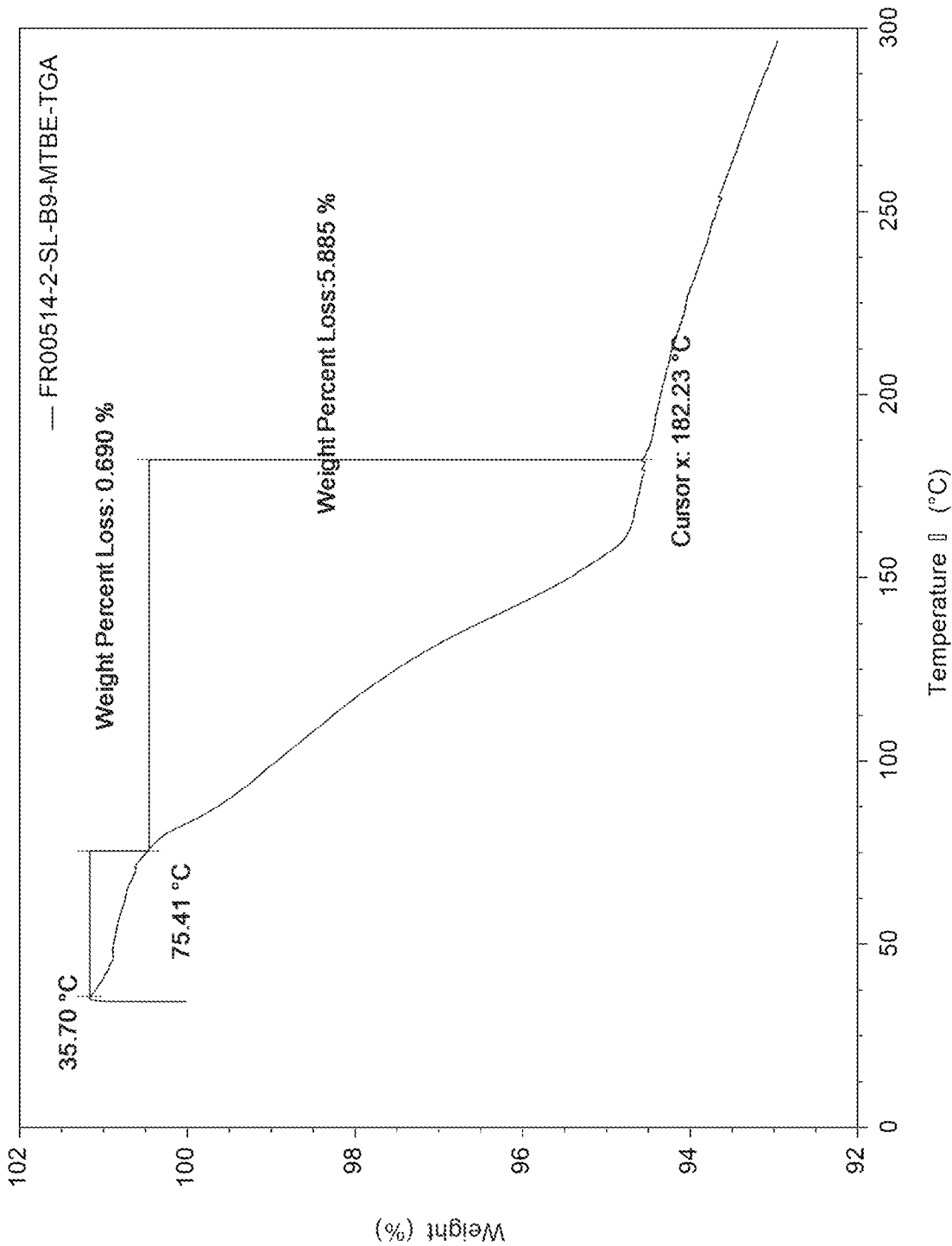
FIG. 6 is a TGA thermogram of polymorphic form C of brequinar sodium salt from batch FR00514-2-SL-B9.

FIG. 6 is a TGA thermogram of polymorphic form C of brequinar sodium salt from batch FR00514-2-SL-B9.

Figure 7:
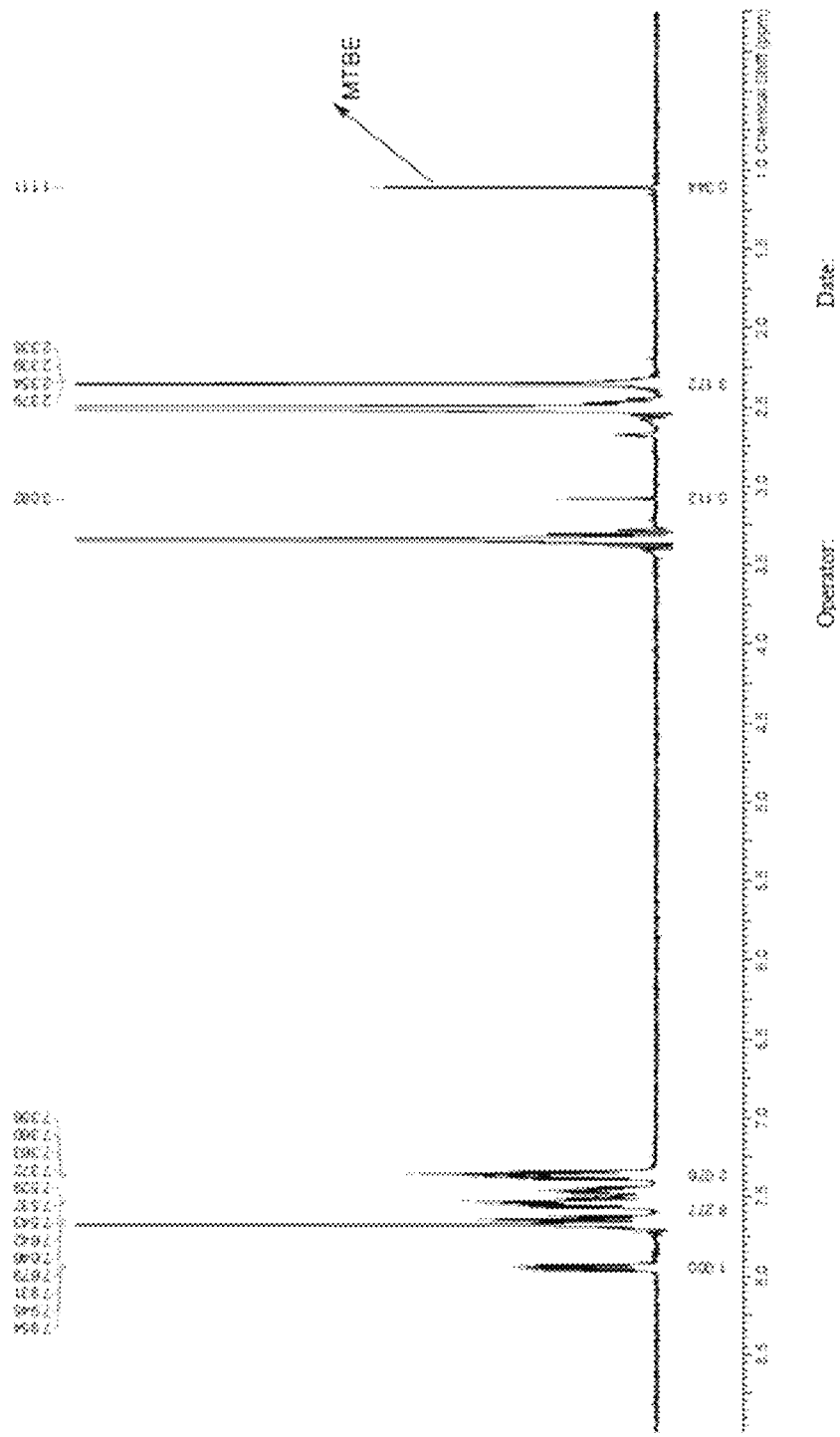
FIG. 7 is a graph of a 1HNMR spectrum of polymorphic form C of brequinar sodium salt from batch FR00514-2-SL-B9.

FIG. 7 is a graph of a 1HNMR spectrum of polymorphic form C of brequinar sodium salt from batch FR00514-2-SL-B9.

Example 2

A general scheme of preparing polymorphic form C of brequinar sodium salt is illustrated in the following schematic:

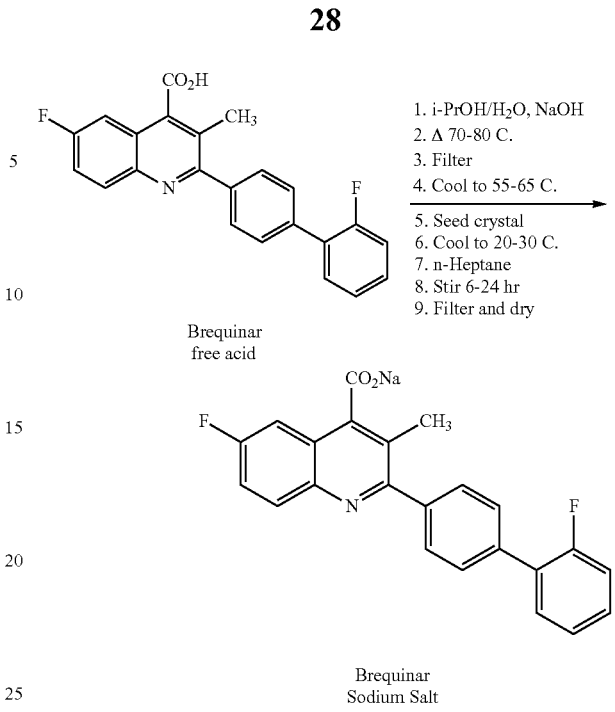

The synthesis of 6-Flouro-2-(2'-fluoro-1,1'-biphenyl-4-yl)-3-methyl-4-quinolinecarboxylic acid sodium salt was carried out by dissolving 6-Flouro-2-(2'-fluoro-1,1'-biphenyl-4-yl)-3-methyl-4-quinolinecarboxylic acid (1.0 eq) in a mixture of isopropanol/water in a ratios of 95/5 to 98/2 with the most desired ratio being 97/3. Sodium hydroxide (1.05 eq) was added and the mixture warmed to a temperature of 70-80° C. until everything was dissolved. The most desired temperature for dissolution is 73-77° C. The mixture was cooled to 55-65° C. and a seed crystal of 6-Flouro-2-(2'-fluoro-1,1'-biphenyl-4-yl)-3-methyl-4-quinolinecarboxylic sodium salt added, cooled to 20-30° C. and n-heptane added. The most desired temperature for addition of n-heptane is 23-27° C. The mixture was then maintained at 20-30° C. and stirred for 6-24 hours. The solid then filtered and dried at 30-50° C.

Example 3

Polymorphic form C of brequinar sodium salt was prepared according to the following scheme. 360.15 g (0.96 mole) of 6-Flouro-2-(2'-fluoro-1,1'-biphenyl-4-yl)-3-methyl-4-quinolinecarboxylic acid was suspended in 2,541 mL of isopropanol and 79 mL of H₂O (97v:3v). 38.80 g (0.97 mole) of sodium hydroxide was added and warmed to 73-77° C. until totally dissolved. The reaction mixture was filtered and then cooled to 57-61° C., and a seed crystal was added. The temperature was adjusted to 23-27° ° C., n-heptane was added, and the mixture was stirred for 24 hours at 23-27° ° C. The solid was then filtered and dried under vacuum at 40° C.

Figure 8:
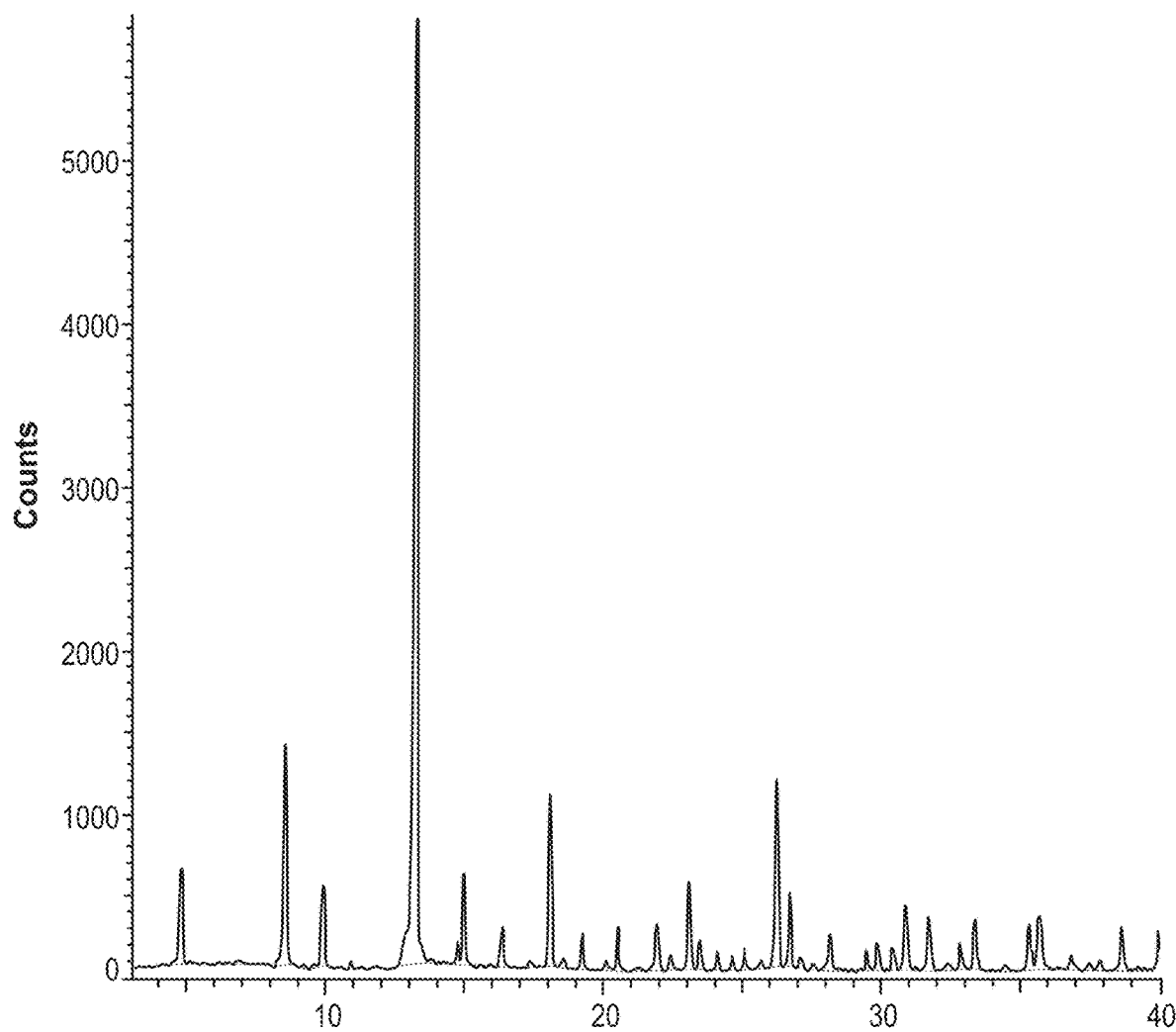
FIG. 8 is an X-ray powder diffraction (XRPD) pattern of the polymorph C form of brequinar sodium salt prepared according to a method of the invention.

FIG. 8 is an X-ray powder diffraction (XRPD) pattern of the polymorph C form of brequinar sodium salt prepared according to this method. The method gave an 88.3% yield of a white crystalline solid. The purity was 99.6%, and the water content by KF (w/w) was 5.2%.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A method of making a crystal comprising at least 80% polymorphic form C of brequinar sodium salt, the method comprising the steps of:
    combining a solid form of brequinar acid, sodium hydroxide (NaOH), and a solvent comprising isopropanol and water to produce a solution and removing insoluble material from the combined brequinar acid, NaOH, and solvent;
    crystallizing brequinar sodium salt from the solution to produce a crystal comprising polymorphic form C of brequinar sodium salt, wherein the crystallizing step comprises sequentially performing the steps of:
        adding a seed crystal of polymorphic form C of brequinar sodium salt to the solution to produce a seeded mixture;
        adding n-heptane to the seeded mixture to produce an alkane-containing mixture and incubating the alkane-containing mixture at from about 15° C. to about 35° C.; and
        removing the solvent from the seeded mixture at a temperature below ambient temperatures, wherein the removing step results in a crystal comprising at least 80% polymorphic form C of brequinar sodium salt as measured by X-ray Diffraction (XRD).

2. The method of claim 1, wherein a ratio of isopropanol:water in the solvent is from about 95:5 to about 98:2.

3. The method of claim 2 wherein the ratio of isopropanol:water in the solvent is about 97:3.

4. The method of claim 1, wherein the NaOH is combined with the brequinar acid at from about 1.0 to about 1.6 molar equivalents.

5. The method of claim 4, wherein the NaOH is combined with the brequinar acid at from about 1.0 to about 1.1 molar equivalents.

6. The method of claim 1, wherein the combining step comprises incubating the combined brequinar acid, NaOH, and solvent at from about 70° C. to about 80° C.

7. The method of claim 1, wherein the combining step comprises incubating the combined brequinar acid, NaOH, and solvent at from about 55° C. to about 65° C.

8. The method of claim 1, wherein the combining step comprises sequentially performing the steps of:
    incubating the combined brequinar acid, NaOH, and solvent at from about 70° C. to about 80° C.;
    removing insoluble material from the combined brequinar acid, NaOH, and solvent; and
    incubating the combined brequinar acid, NaOH, and solvent at from about 55° C. to about 65° ° C.

9. The method of claim 1, wherein the crystallizing step comprises incubating the seeded mixture at from about 20° C. to about 30° C.

10. The method of claim 1, wherein the crystallizing step comprises incubating the alkane-containing mixture for from about 6 hours to about 24 hours.

11. The method of claim 1, further comprising sequentially performing the steps of:
    incubating the alkane-containing mixture for from about 6 hours to about 24 hours; and
    removing the solvent from polymorphic form C of brequinar sodium salt.

12. The method of claim 1, wherein the removing step results in a crystal comprising at least 85% polymorphic form C of brequinar sodium salt as measured by XRD.

13. The method of claim 1, wherein the removing step results in a crystal comprising at least 90% polymorphic form C of brequinar sodium salt as measured by XRD.

14. The method of claim 1, wherein the removing step results in a crystal comprising at least 95% polymorphic form C of brequinar sodium salt as measured by XRD.

* * * * *